US 8,158,375 B2

(12) United States Patent
Itai et al.

(10) Patent No.: US 8,158,375 B2
(45) Date of Patent: Apr. 17, 2012

(54) POLYMER AND METHOD OF MEASURING CHOLESTEROL THEREWITH

(75) Inventors: Tomokazu Itai, Amagasaki (JP); Kiyoko Mori, Amagasaki (JP); Yo Yagura, Amagasaki (JP); Isao Koyama, Amagasaki (JP); Naoyuki Yamamoto, Amagasaki (JP)

(73) Assignee: Wako Pure Chemical Industries, Ltd., Osaka (JP)

( * ) Notice: Subject to any disclaimer, the term of this patent is extended or adjusted under 35 U.S.C. 154(b) by 725 days.

(21) Appl. No.: 11/988,475

(22) PCT Filed: Mar. 14, 2006

(86) PCT No.: PCT/JP2006/304971
§ 371 (c)(1),
(2), (4) Date: Feb. 23, 2009

(87) PCT Pub. No.: WO2007/007443
PCT Pub. Date: Jan. 18, 2007

(65) Prior Publication Data
US 2009/0215097 A1 Aug. 27, 2009

(30) Foreign Application Priority Data
Jul. 11, 2005 (WO) .................. PCT/JP2005/012777

(51) Int. Cl.
C12Q 1/60 (2006.01)
(52) U.S. Cl. ........................................... 435/11
(58) Field of Classification Search ............ 435/11
See application file for complete search history.

(56) References Cited

U.S. PATENT DOCUMENTS

| | | | |
|---|---|---|---|
| 5,773,304 A | | 6/1998 | Hino et al. |
| 5,888,755 A | * | 3/1999 | Miyauchi et al. ............... 435/11 |
| 5,925,534 A | | 7/1999 | Miki et al. |
| 6,114,134 A | | 9/2000 | Kishi et al. |
| 6,162,607 A | | 12/2000 | Miki et al. |
| 6,194,164 B1 | | 2/2001 | Matsui et al. |
| 6,362,276 B1 | * | 3/2002 | Harris et al. ................. 525/54.1 |
| 2002/0001819 A1 | | 1/2002 | Matsui et al. |

FOREIGN PATENT DOCUMENTS

| | | |
|---|---|---|
| EP | 0699767 | 6/1996 |
| JP | 2600065 | 1/1997 |
| JP | 9-121895 | 5/1997 |
| JP | 9-121895 A | 5/1997 |
| JP | 2799835 | 7/1998 |
| JP | 2000-60600 | 2/2000 |
| JP | 3058602 | 4/2000 |
| JP | 2001-17197 | 1/2001 |
| JP | 3164829 | 3/2001 |
| JP | 2001-124780 | 5/2001 |
| JP | 3193634 | 5/2001 |
| JP | 2001-201503 | 7/2001 |
| JP | 2001-288233 | 10/2001 |
| JP | 2001-288233 A | 10/2001 |
| JP | 3446486 | 7/2003 |
| JP | 2005-100966 | 4/2005 |
| WO | 98/59068 | 12/1998 |

OTHER PUBLICATIONS

Chern et al. "Synthesis and characterization of amphiphilic graft copolymers with poly(ethylene glycol) and cholesterol side chains", Polymer International, 2004, 53:420-429.*
Lipoprotein classification: 1 page, 2011.*
Izzo et al. "Improved method for determination of high-density-lipoprotein cholesterol I. isolation of HDL by usde of polyethylene glycol 6000", Clin. Chem. 1981, 27(3):371-374.*
Office Action issued by the European Patent Office in co-pending European Application No. 06 729 024.7, dated Oct. 20, 2009.

* cited by examiner

*Primary Examiner* — Sue Liu
*Assistant Examiner* — Bin Shen
(74) *Attorney, Agent, or Firm* — Hamre, Schumann, Mueller & Larson, P.C.

(57) ABSTRACT

It is an object of the present invention to provide the method for determining cholesterol in lipoprotein and reagent for determining cholesterol comprising the polymer, and the present invention relates to the reagent for determining cholesterol in lipoproteins such as high-density lipoprotein (HDL), low-density lipoprotein (LDL) and very low-density lipoprotein (VLDL) and the determination method using the polymer comprising the following units as constituents:
(iv) a polyethylene glycol segment represented by the general formula [1]:

$$—(CH_2CH_2O)k—$$ [1]

(wherein, k represents an integer of 10 to 250);
(v) a monomer unit represented by the general formula [2]:

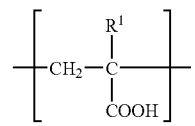

[2]

(wherein $R^1$ represents a hydrogen atom or $C_1$-$C_3$ alkyl group); and
(vi) a monomer unit represented by the general formula [3]:

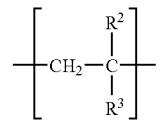

[3]

[wherein, $R^2$ represents a hydrogen atom or $C_1$-$C_3$ alkyl group, and $R^3$ represents a group represented by the general formula [4]:

$$—COOR^4$$ [4]

(wherein, $R^4$ represents an alkyl group, a haloalkyl group or a bornyl group), an alkyl group, an alkoxy group, an aralkyl group or an alkylcarbamoyl group; particularly, in the direct measurement of cholesterols such as HDL, LDL and VLDL contained in the sample, the reagent for determining cholesterol in the presence of said polymer, and the method for determining the concentration of cholesterol in a specific lipoprotein using said reagent for determining cholesterol, and a novel polymer.

13 Claims, 5 Drawing Sheets

[Figure 1]
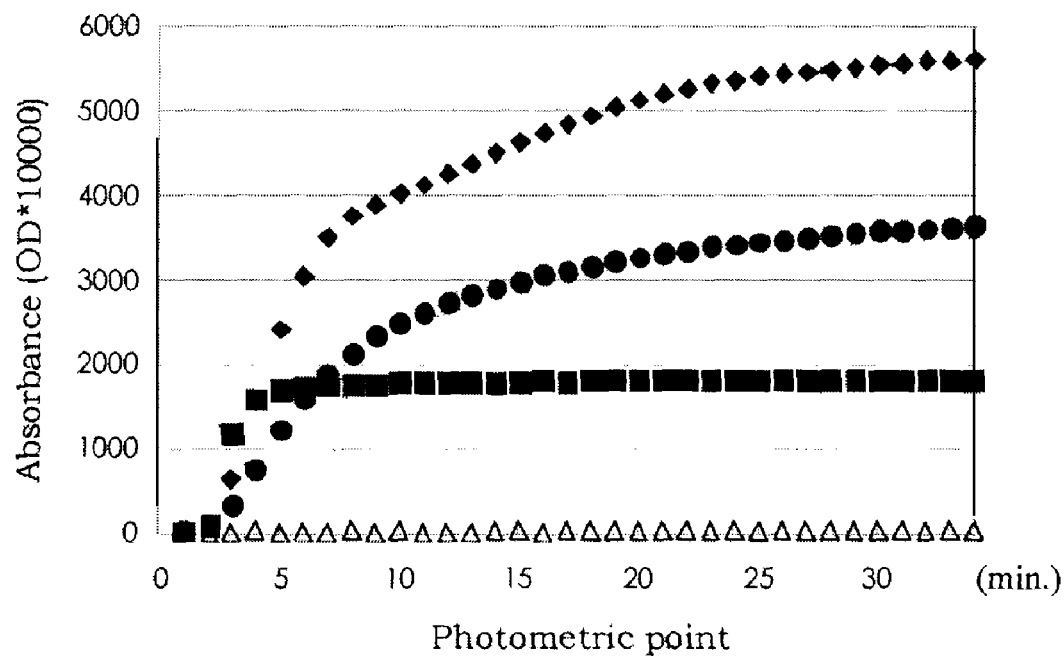
[Figure 2]
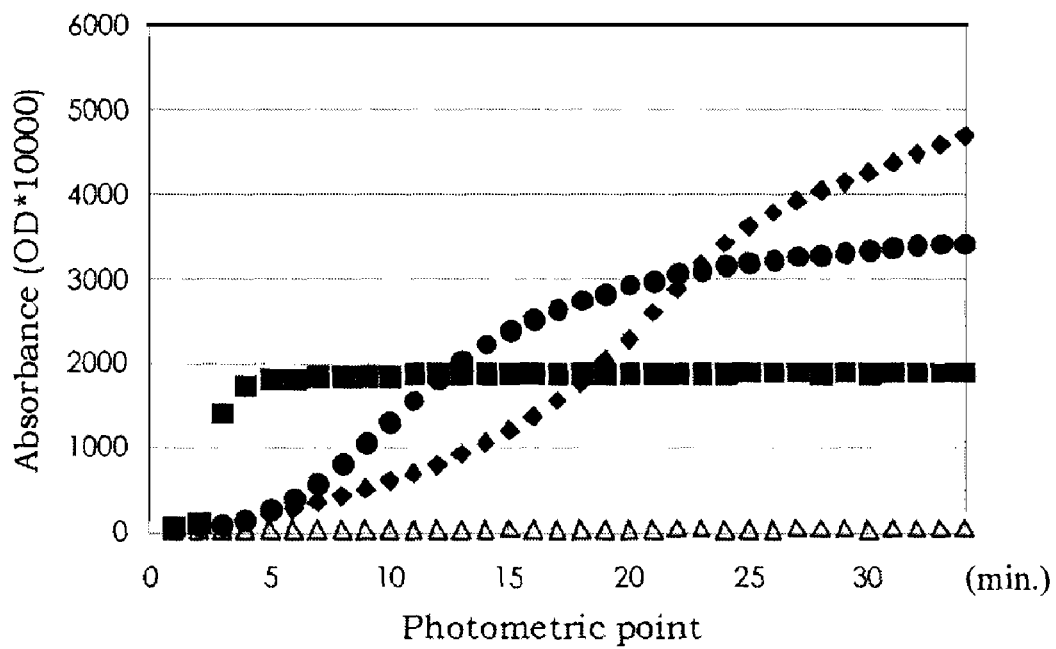

[Figure 3]
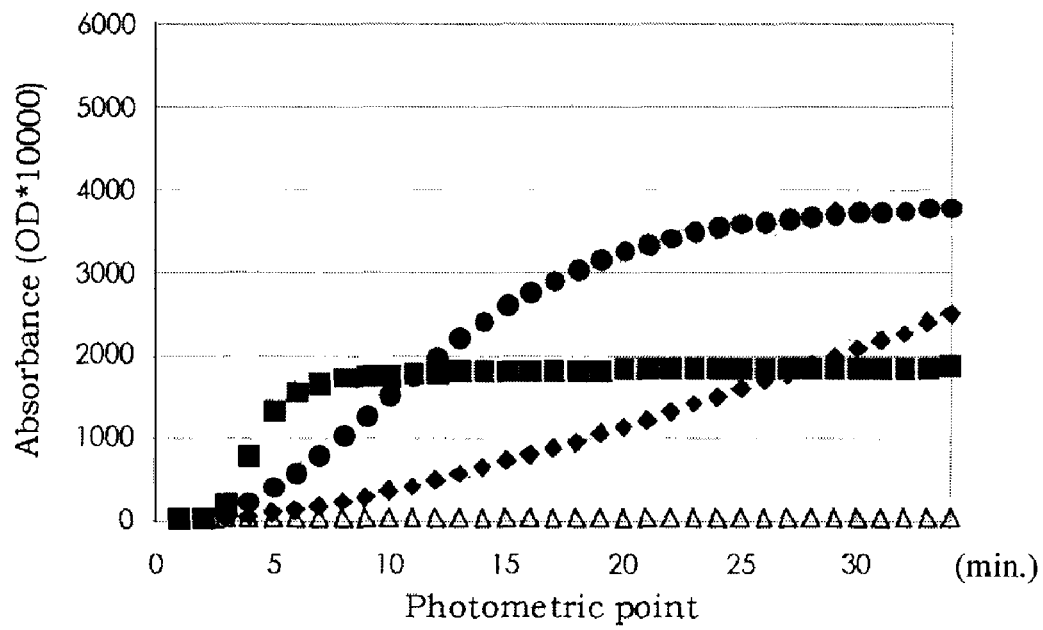
[Figure 4]
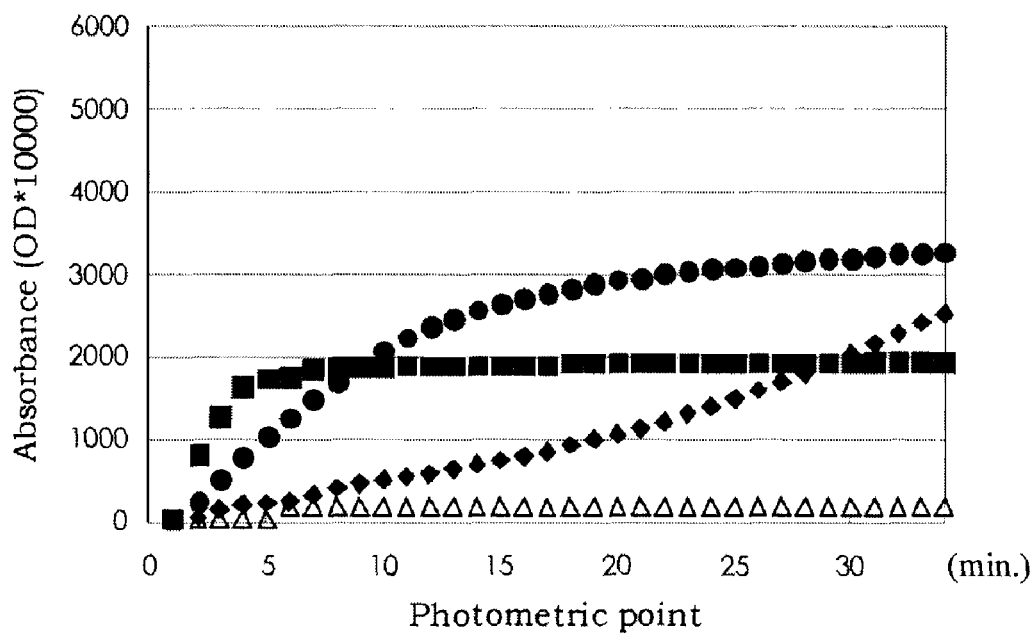

[Figure 5]
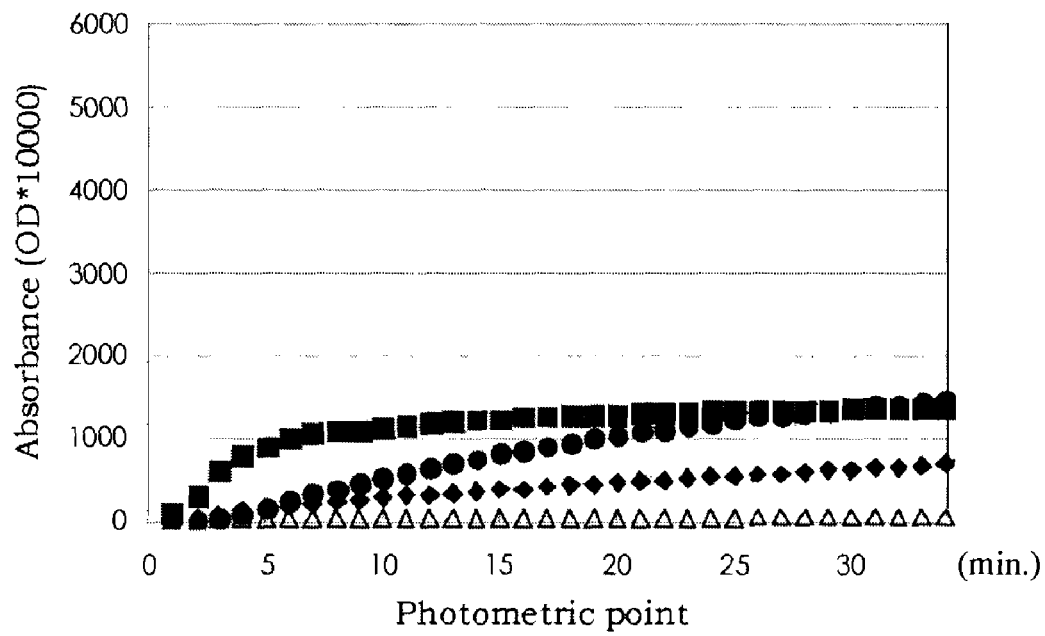
[Figure 6]
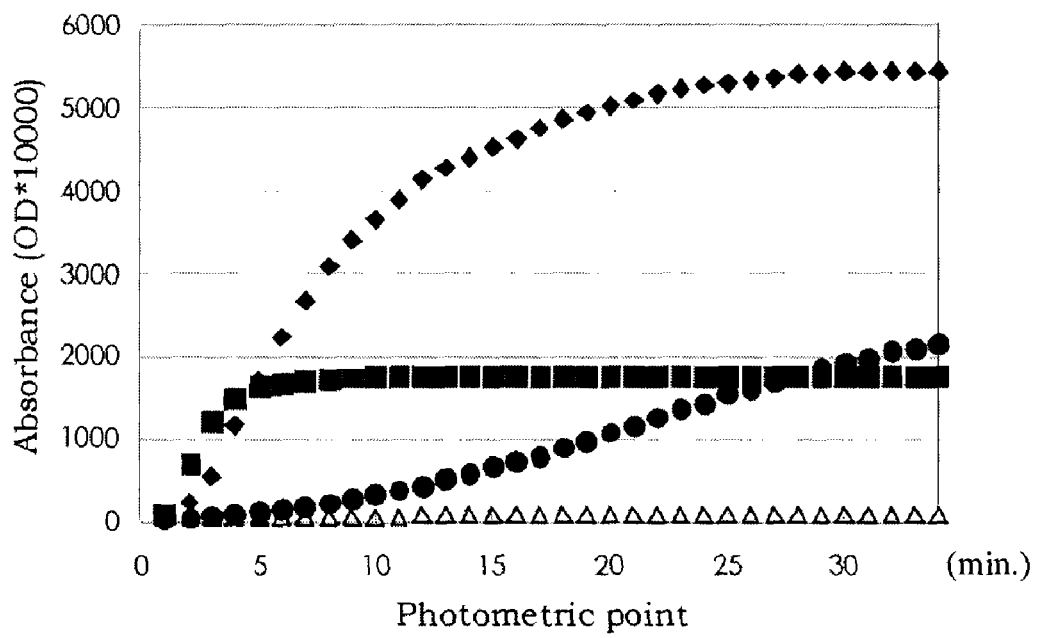

[Figure 7]
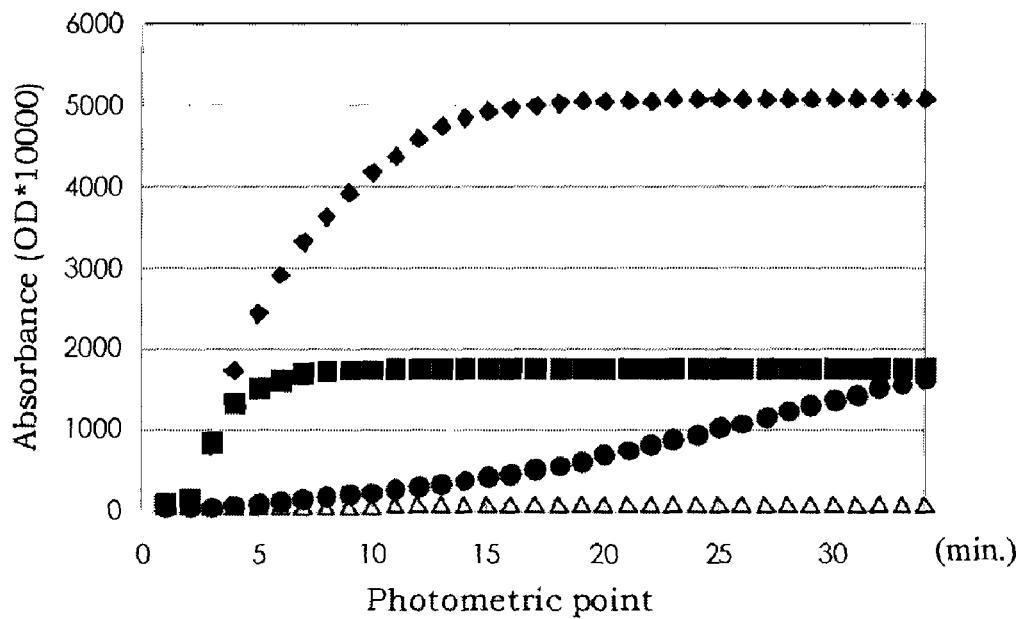
[Figure 8]
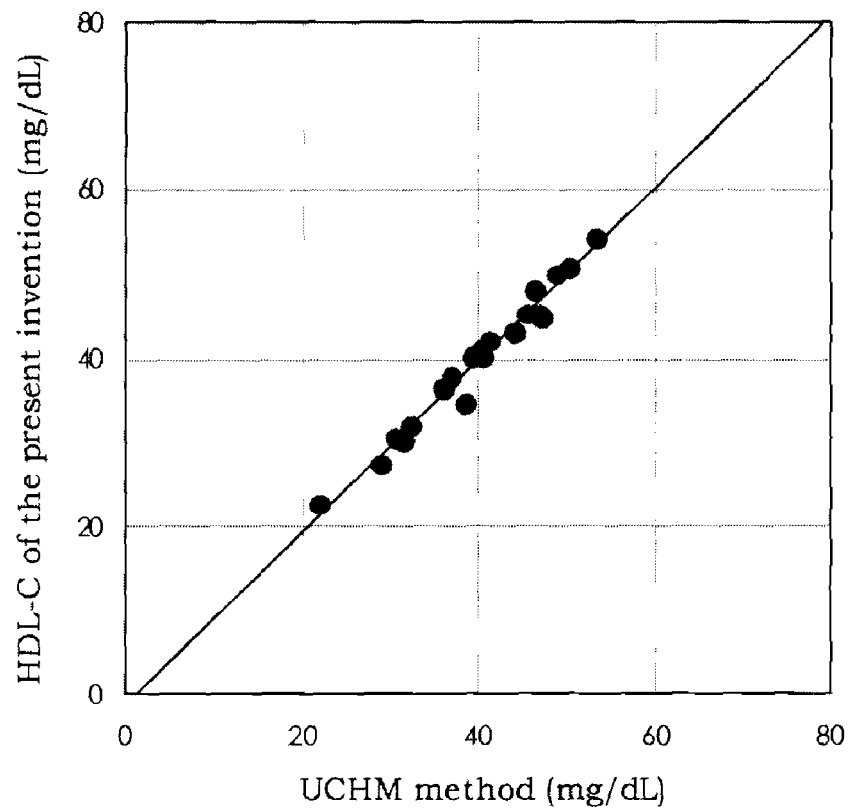

[Figure 9]
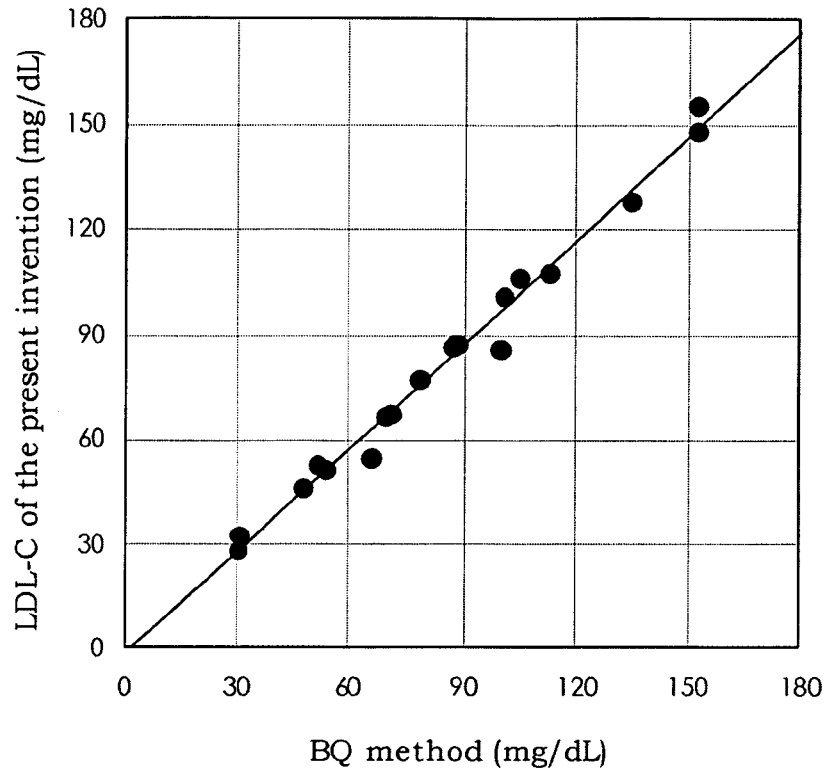
[Figure 10]
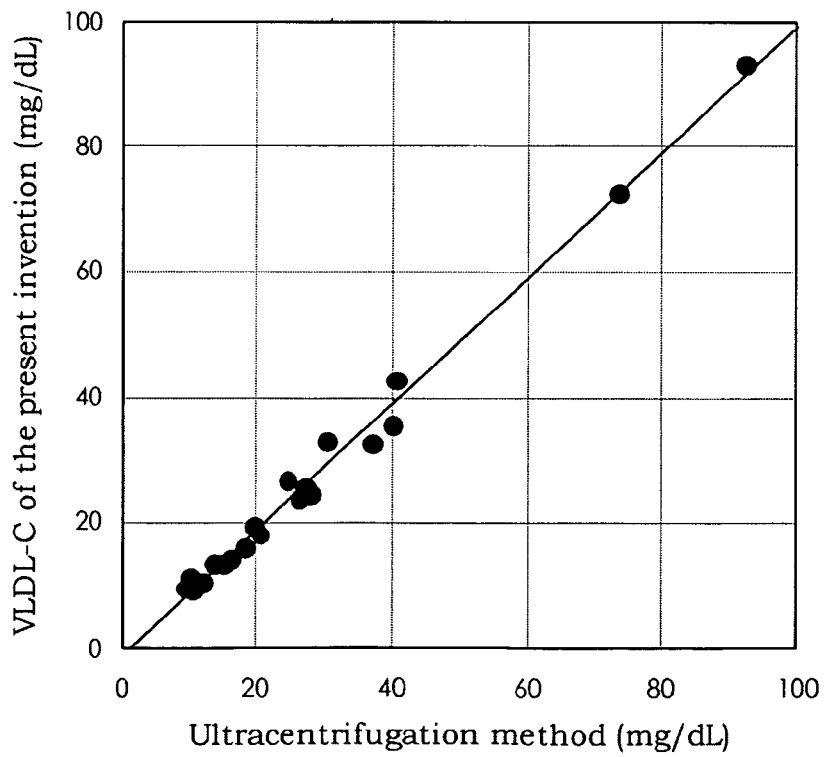

POLYMER AND METHOD OF MEASURING CHOLESTEROL THEREWITH

TECHNICAL FIELD

The present invention relates to a reagent, a kit and a method for determining cholesterol in the lipoproteins such as high density lipoprotein (HDL), low density lipoprotein (LDL) and very low density lipoprotein (VLDL), using a polymer comprising a polyethylene glycol segment having a group shown in general formula [1], a monomer unit shown in the general formula [2] and a monomer unit shown in the general formula [3] as constituents; for details, in the direct determination of cholesterol in HDL, LDL and VLDL in a sample, a reagent and a kit for determining cholesterol in the lipoprotein in coexistence of the aforementioned polymer and a method for determining the cholesterol concentration in a specified lipoprotein using aforementioned reagent for the measurement, and relates to a polymer comprising a polyethylene glycol segment having a group shown in the general formula [1], a monomer unit shown in the general formula [2] and the third monomer unit.

BACKGROUND ART

The determination of cholesterol in the lipoprotein in the serum and the plasma is utilized mainly for the diagnosis of arteriosclerosis, cardiomyopathy and lipid abnormality analysis, and is one of important measurement items in the clinical laboratory test field. Particularly, as to the measurement of HDL cholesterol (HDL-C) and LDL cholesterol (LDL-C), a guideline has been established by Japan Atherosclerosis Society, and is one of the high-frequency measurement items. A method for the direct determination of HDL-C which may be carried out using an automated analyzer without conducting centrifugal separation operation, includes, for example, a method of detecting only HDL-C by protecting lipoproteins other than HDL using anti β-lipoprotein antibody (Patent Literature 1); a method of detecting only HDL-C using a sugar compound such as cyclodextrin derivatives and a modified enzyme (Patent Literature 2); a method using a surface-active agent which does not dissolve lipoprotein (Patent Literature 3); a method of specifically-detecting HDL-C after elimination of cholesterol in the lipoprotein other than HDL (Patent Literature 4); and a method of detecting HDL-C, in which the lipoproteins other than HDL is protected by forming complex using calixarenes (Patent Literature 5).

On the other hand, a method for the direct determination of LDL-C which may be carried out and using an automated analyzer without conducting centrifugal separation operation, includes, a method for measurement of LDL-C, after protecting the LDL with polyanion and a ampholytic surface-active agent, and eliminating cholesterol in the lipoprotein other than LDL (Patent Literature 6); a method for measurement of the LDL-C after solubilizing and eliminating only lipoprotein other than LDL using a surface-active agent (Patent Literature 7 and Patent Literature 8); and a method for measurement of the LDL-C by protecting the lipoprotein other than LDL using calixarenes (Patent Literature 9).

However, the measurement precision of these reagents is satisfiable for a specimen having lipid concentration within normal range (normolipemic specimen), but for a specimen with lipid abnormality such as, for example, high triglyceride (TG) specimen, these reagents are not exactly sufficient with respect to accuracy of the measurement value compared with those obtained by standard determination method such as UCHM method, which are in combination with the fractionation by ultracentrifugation (Ultracentrifugation-heparin-$MnCl_2$-method), or BQ method (Beta-Quantification method). This is the present situation. In addition, a block copolymer having polyethylene glycol in main chain and the use thereof as a cosmetic have been disclosed in Patent Literature 10.

Patent Literature 1: JP-B-3446486.
Patent Literature 2: JP-B-2600065.
Patent Literature 3: JP-B-2799835.
Patent Literature 4: JP-B-3164829.
Patent Literature 5: WO98/59068.
Patent Literature 6: JP-A-2000-60600.
Patent Literature 7: JP-B-3193634.
Patent Literature 8: JP-B-3058602.
Patent Literature 9: WO98/59068.
Patent Literature 10: JP-A-2001-288233.

DISCLOSURE OF INVENTION

Problem to be Solved by the Invention

It is an object of the present invention to provide a method for determining cholesterol in the lipoprotein with comprising a polymer and a reagent for determination, and a novel polymer.

Means for Solving the Problem

The present invention relates to
(1) a polymer (hereinafter, it may be abbreviated as "polymer (a) of the present invention") comprising the following segment and monomer units as constituents:
(i) a polyethylene glycol segment having a group represented by the general formula [1];

[1]

(wherein, k represents an integer of 10 to 250);
(ii) a monomer unit represented by the general formula [2];

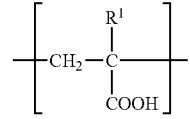

[2]

(wherein, $R^1$ represents a hydrogen atom or $C_1$-$C_3$ alkyl group); and
(iii) a third monomer unit derived from tert-butyl methacrylate, cyclohexyl methacrylate, 2-ethylhexyl methacrylate, dodecyl methacrylate, bornyl methacrylate, di(trifluoromethyl)methyl methacrylate, 2,2,3,3,4,4,5,5-octafluoropentyl methacrylate, heptadecafluorooctylethyl methacrylate, cyclohexyl methacrylamide, cyclohexyl acrylate, vinylcyclohexyl, allylcyclohexyl, cyclohexylvinyl ether or allylbenzene;
(2) a determination method of cholesterol in a specific lipoprotein, which comprises determining the amount of cholesterol in coexistence of the following polymer (hereinafter, it may be abbreviated as "polymer relevant to the present invention"):

a polymer comprising the following segment and monomer units as constituents:
(iv) a polyethylene glycol segment having a group represented by the general formula [1];

—(CH$_2$CH$_2$O)$k$—      [1]

(wherein, k is the same as described the above);
(v) a monomer unit represented by the general formula [2];

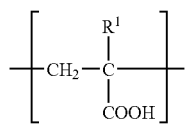
[2]

(wherein, R$^1$ is the same as described the above); and
(vi) a monomer unit represented by the general formula [3]:

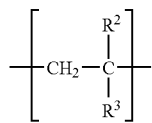
[3]

(wherein, R$^2$ represents a hydrogen atom or C$_1$-C$_3$ alkyl group, R$^3$ represents a group represented by the general formula [4];

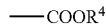
—COOR$^4$      [4]

(wherein, R$^4$ represents an alkyl group, a haloalkyl group or a bornyl group); an alkyl group, an alkoxy group, an aralkyl group or an alkylcarbamoyl group; and
(3) a reagent for determining cholesterol in the specified lipoprotein in a biological sample, which comprises the polymer containing the above described (iv) to (vi) as constituents in a reagent for determining cholesterol based on the amount of hydrogen peroxide or NAD(P)H [reduced nicotinamide adenine dinucleotide (phosphate)] generated by the reaction of the biological sample with (1) cholesterol esterase (CHE) and cholesterol oxidase (CO), or with (2) CHE, cholesterol dehydrogenase (CHD) and NAD(P) [nicotinamide adenine dinucleotide (phosphate)];
(4) a reagent for determining cholesterol in the specified lipoprotein in the biological sample, which comprises the polymer containing the above described (iv) to (vi) as constituents in the reagent for determining cholesterol based on the amount of hydrogen peroxide or NAD(P)H generated by the reaction of the cholesterol in the specified lipoprotein with (1) CHE and CO, or with (2) CHE, CHD and NAD(P), after eliminating the cholesterol in the lipoprotein other than the specified lipoprotein by contacting the biological sample with a reagent for eliminating cholesterol in the lipoprotein other than the specified lipoprotein;
(5) a kit for determining cholesterol in a specified lipoprotein, which comprises the first reagent solution containing (1) a polymer comprising the above described (iv) to (vi) as constituents, (2) CHE, (3) CO, peroxidase (POD) and a coupler or/and a developer, and (4) aqueous medium, and the second reagent solution containing (5) CHE, (6) CO and (7) aqueous medium, wherein each of POD, a coupler, a developer may be contained in the second reagent solution;
(6) a kit for determining cholesterol in the specified lipoprotein, which comprises the first reagent solution containing (1) a polymer comprising the above described (iv) to (vi) as constituents, (2) CHE, (3) CO, (4) POD, (5) a coupler (6) a developer and (7) aqueous medium, and the second reagent solution containing (8) surface-active agent and (9) aqueous medium; and
(7) a kit for determining cholesterol in the specified lipoprotein, which comprises the first reagent solution containing (1) a polymer comprising the above described (iv) to (vi) as constituents, (2) CHE, (3) CO, (4) catalase (CAT) and (5) aqueous medium, and the second reagent solution containing (6) CAT inhibitor, (7) aqueous medium and if needed (8) surface-active agent, wherein POD, a coupler, a developer are each contained in at least one of the first reagent solution or the second reagent solution.

Effect of the Invention

In the method for the direct determination of cholesterol in the lipoprotein, the reaction of the cholesterol in the lipoprotein other than the specified lipoprotein is preceded preferentially by protecting a specified lipoprotein and inhibiting, in other words, delaying or stopping temporarily, the reaction of cholesterol in the aforementioned specified lipoprotein, in the coexistence of a polymer (hereinafter, optionally may be abbreviated said polymer as "the polymer relevant to the present invention") comprising above described (iv) polyethylene glycol segment having a group shown in the general formula [1], (v) a monomer unit shown in the general formula [2] and (vi) a monomer unit shown in the general formula [3] as constituents, especially with a polymer (hereinafter, optionally may be abbreviated said polymer as "the polymer (a) of the present invention") consisting of the above described (i) a polyethylene glycol segment having a group shown in the general formula [1], (ii) a monomer unit shown in the general formula [2] and (iii) a third monomer unit.

Further, the cholesterol in the specified lipoprotein can be determined by eliminating the cholesterol in the lipoprotein other than said specified lipoprotein, in which the reaction was preceded.

By this procedure, the cholesterol in the objective lipoprotein can be determined without conducting separation and segregation of the lipoprotein other than the objective lipoprotein as the determination target. Further, according to the present invention, it may be possible to provide a method and a reagent for determining cholesterol in the lipoprotein with excellent measurement accuracy in accord with the measurement value obtained by the standard determination method even for problematic measurement value of specimen with lipid abnormality.

BEST MODE FOR CARRYING OUT THE INVENTION

1. Polymer Relevant to the Present Invention
1-1. Polymer
In the general formula [1], k is usually an integer of 10 to 250, preferably 20 to 200, more preferably 40 to 150.
In the general formula [2] and [3], C$_1$-C$_3$ alkyl group represented by R$^1$ and R$^2$ may be straight chained or branched, and includes usually C$_1$-C$_3$ alkyl group having, preferably C$_1$ alkyl group, which is specifically exemplified by, for example, a methyl group, an ethyl group a n-propyl group or an isopropyl group, in particular, a methyl group is preferable.

In the general formula [3], the alkyl group represented by $R^3$ may be straight chained, branched or cyclic, and includes usually $C_1$-$C_{15}$ alkyl group, preferably $C_3$-$C_8$ alkyl group, which is specifically exemplified by, for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a n-hexyl group, an isohexyl group, a sec-hexyl group, a tert-hexyl group, a neohexyl group, a n-heptyl group, an isoheptyl group, a sec-heptyl group, a tert-heptyl group, a neoheptyl group, a n-octyl group, an isooctyl group, a sec-octyl group, a tert-octyl group, a neooctyl group, a n-nonyl group, an isononyl group, a sec-nonyl group, a tert-nonyl group, a neononyl group, a n-decyl group, an isodecyl group, a sec-decyl group, a tert-decyl group, neodecyl group, a n-undecyl group, an isoundecyl group, a sec-undecyl group, a tert-undecyl group, a neoundecyl group, a n-dodecyl group, an isododecyl group, a sec-dodecyl group, a tert-dodecyl group, a neododecyl group, a n-tridecyl group, an isotridecyl group, a sec-tridecyl group, a tert-tridecyl group, a neotridecyl group, a n-tetradecyl group, an isotetradecyl group, a sec-tetradecyl group, a tert-tetradecyl group, a neotetradecyl group, a n-pentadecyl group, an isopentadecyl group, a sec-pentadecyl group, a tert-pentadecyl group, a neopentadecyl group, a cyclopropyl group, a cyclobutyl group, a cyclopentyl group, a cyclohexyl group, a cyclohexylmethyl group, a cycloheptyl group, a cyclooctyl group, a cyclononyl group, a cyclodecyl group, a cycloundecyl group, a cyclododecyl group, a cyclotridecyl group, a cyclotetradecyl group or a cyclopentadecyl group, in particular, a cyclohexyl group or a cyclohexylmethyl group is preferable.

The alkoxy group represented by $R^3$ may be straight chained, branched or cyclic, and includes usually $C_1$-$C_{10}$ alkoxy group, preferably $C_1$-$C_6$ alkoxy group, which is specifically exemplified by, for example, a methoxy group, an ethoxy group, a n-propoxy group, an isopropoxy group, a n-butoxy group, an isobutoxy group, a sec-butoxy group, a tert-butoxy group, a n-pentyloxy group, an isopentyloxy group, a sec-pentyloxy group, a tert-pentyloxy group, a neopentyloxy group a n-hexyloxy group, an isohexyloxy group, a sec-hexyloxy group, a tert-hexyloxy group, a neohexyloxy group, a n-heptyloxy group, an isoheptyloxy group, a sec-heptyloxy group, a tert-heptyloxy group, a neoheptyloxy group, a n-octyloxy group, an isooctyloxy group, a sec-octyloxy group, a tert-octyloxy group a neooctyloxy group, a n-nonyloxy group, an isononyloxy group, a sec-nonyloxy group, a tert-nonyloxy group, a neononyloxy group, a n-decyloxy group, an isodecyloxy group, a sec-decyloxy group, a tert-decyloxy group, a neodecyloxy group, a cyclopropoxy group, a cyclobutoxy group, a cyclopentyloxy group, a cyclohexyloxy group, a cycloheptyloxy group, a cyclooctyloxy group, a cyclononyloxy group or a cyclodecyloxy group, in particular, a cyclohexyloxy group is preferable.

The aralkyl group represented by $R^3$ includes usually $C_7$-$C_{12}$ aralkyl group, which is specifically exemplified by, for example, a benzyl group, a phenylpropyl group, a phenylbutyl group, a phenylpentyl group or a phenylhexyl group, in particular, a benzyl group is preferable.

The alkylcarbamoyl group represented by $R^3$ may be straight chained, branched or cyclic, and includes usually $C_2$-$C_{11}$ alkylcarbamoyl group, preferably $C_2$-$C_7$ alkylcarbamoyl group, which is specifically exemplified by, for example, a methylcarbamoyl group, an ethylcarbamoyl group, a n-propylcarbamoyl group, an isopropylcarbamoyl group, a n-butylcarbamoyl group, an isobutylcarbamoyl group, a sec-butylcarbamoyl group, a tert-butylcarbamoyl group, a n-pentylcarbamoyl group, an isopentylcarbamoyl group, a sec-pentylcarbamoyl group, a tert-pentylcarbamoyl group, a neopentylcarbamoyl group, a n-hexylcarbamoyl group, an isohexylcarbamoyl group, a sec-hexylcarbamoyl group, a tert-hexylcarbamoyl group, a neohexylcarbamoyl group, a n-heptylcarbamoyl group, an isoheptylcarbamoyl group, a sec-heptylcarbamoyl group, a tert-heptylcarbamoyl group, a neoheptylcarbamoyl group, a n-octylcarbamoyl group, an isooctylcarbamoyl group, a sec-octylcarbamoyl group, a tert-octylcarbamoyl group, a neooctylcarbamoyl group, a n-nonylcarbamoyl group, an isononylcarbamoyl group, a sec-nonylcarbamoyl group, a tert-nonylcarbamoyl group, a neononylcarbamoyl group, a n-decylcarbamoyl group, an isodecylcarbamoyl group, a sec-decylcarbamoyl group, a tert-decylcarbamoyl group, a neodecylcarbamoyl group, a cyclopropylcarbamoyl group, a cyclobutylcarbamoyl group, a cyclopentylcarbamoyl group, a cyclohexylcarbamoyl group, a cyclohexylmethylcarbamoyl group, a cycloheptylcarbamoyl group, a cyclooctylcarbamoyl group, a cyclononylcarbamoyl group or a cyclodecylcarbamoyl group, in particular, a cyclohexylcarbamoyl group is preferable.

In the general formula [4], the alkyl group represented by $R^4$ may be straight chained, branched or cyclic, and includes usually $C_1$-$C_{15}$ alkyl group, preferably $C_3$-$C_{12}$ alkyl group, which is specifically exemplified by, for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a n-hexyl group, an isohexyl group, a sec-hexyl group, a tert-hexyl group, a neohexyl group, a 3-methylpentyl group, a 2-methylpentyl group, a 1,2-dimethylbutyl group, a n-heptyl group, an isoheptyl group, a sec-heptyl group, a tert-heptyl group, a neoheptyl group, a n-octyl group, an isooctyl group, a sec-octyl group, a tert-octyl group, a neooctyl group, a 2-ethylhexyl group, a nonyl group, a decyl group, an undecyl group, a dodecyl group, a tridecyl group, a tetradecyl group, a pentadecyl group, a cyclopropyl group, a cyclopentyl group, a cyclohexyl group, a cyclohexylmethyl group, a cycloheptyl group, a cyclooctyl group, a cyclononyl group, a cyclodecyl group, a cyclododecyl group, a cycloundecyl group, a cyclotridecyl group, a cyclotetradecyl group or a cyclopentadecyl group, in particular, for example, a tert-butyl group, a cyclohexyl group, a 2-ethylhexyl group or a n-dodecyl group is preferable.

The haloalkyl group represented by $R^4$ includes the group wherein a part or all hydrogen atoms of $C_1$-$C_{12}$ alkyl group are substituted with halogen atoms (e.g. fluorine atom, bromine atom, chlorine atom or an iodine atom is included, in particular, fluorine atom is preferable), and includes, usually $C_1$-$C_{12}$ haloalkyl group, preferably $C_1$-$C_{10}$ haloalkyl group, which is specifically exemplified by, for example, a fluoromethyl group, a chloromethyl group, a bromomethyl group, a iodomethyl group, a trifluoromethyl group, a trichloromethyl group, a tribromomethyl group, a 2-fluoroethyl group, a 2-chloroethyl group, a 2-bromoethyl group, a 3-fluoropropyl group, a 3-chloropropyl group, a 3-bromopropyl group, a trifluoropropyl group, a trichloropropyl group, a tribromopropyl group, a di(trifluoromethyl)methyl group, a di(trichloromethyl)methyl group, a di(tribromomethyl)methyl group, a heptafluoropropyl group, a heptachloropropyl group, a 4-fluorobutyl group, a 4-chlorobutyl group, a 4-bromobutyl group, a nonafluorobutyl group, a nonachlorobutyl group, a nonabromobutyl group, a 5-fluoropentyl group, a 5-chloropentyl group, a 5-bromopentyl group, a 2,2,3,3,4,4, 5,5-octafluoropentyl group (—CH$_2$(CF$_2$)$_4$H), a 2,2,3,3,4,4,5, 5-octachloropentyl group (—CH$_2$(CCl$_2$)$_4$H), a 2,2,3,3,4,4,5, 5-octabromopentyl group (—CH$_2$(CBr$_2$)$_4$H), a perfluoropentyl group, a perchloropentyl group, a perbromopentyl group, a 6-fluorohexyl group, a 6-chlorohexyl group, a 6-bromohexyl group, a perfluorohexyl group, a perchlorohexyl group, a perbromohexyl group, a perfluoroheptyl group, a perchloroheptyl group, a perbromoheptyl group, a perfluorooctyl group, a perchlorooctyl group, a perbromooctyl group, a perfluorononyl group, a perchlorononyl group, a perbromononyl group, a heptadecafluorooctylethyl group (—(CH$_2$)$_2$(CF$_2$)$_7$CF$_3$), a heptadecachlorooctylethyl group (—(CH$_2$)$_2$(CCl$_2$)$_7$CCl$_3$), a heptadecabromooctylethyl group (—(CH$_2$)$_2$(CBr$_2$)$_7$CBr$_3$), a perfluorodecyl group, a perchlorodecyl group, a perbromodecyl group, a perfluoroundecyl group, a perchloroundecyl group, a perbromoundecyl group, a perfluorododecyl group, a perchlorododecyl group or a perbromododecyl group, in particular, for example, di(trifluoromethyl)methyl group, a 2,2,3,3,4,4,5,5-octafluoropentyl group or a heptadecafluorooctylethyl group is preferable.

The polyethylene glycol segment represented by the general formula [1] includes, for example, one represented by the general formula [5]:

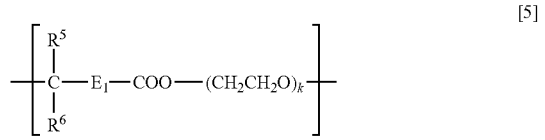

(wherein, R$^5$ represents a hydrogen atom or C$_1$-C$_3$ alkyl group, R$^6$ represents a cyano group or C$_1$-C$_3$ alkyl group, E$_1$ represents C$_1$-C$_6$ alkylene group, and k is an integer of 10-250).

In the general formula [5], C$_1$-C$_3$ alkyl group represented by R$^5$ and R$^6$ may be straight chained or branched, and includes usually C$_1$-C$_3$ alkyl group, preferably C$_1$ alkyl group, which is specifically exemplified by, for example, a methyl group, an ethyl group, a n-propyl group or an isopropyl group, in particular, a methyl group is preferable.

In particular, either of R$^5$ and R$^6$ is preferably a cyano group.

C$_1$-C$_6$ alkylene group represented by E$_1$ may be straight chained or branched, and includes usually C$_1$-C$_6$ alkylene group, preferably C$_1$-C$_4$ alkylene group, more preferably C$_2$ alkylene group, which is specifically exemplified by, for example, straight chain alkylene groups such as a methylene group, an ethylene group, a trimethylene group, a tetramethylene group, a pentamethylene group and a hexamethylene group; branched alkylene groups such as, for example, an ethylidene group, a propylene group, an isopropylidene group, an ethylethylene group, a 1-methyltrimethylene group, a 2-methyltrimethylene group, a 1-methyltetramethylene group, a 2-methyltetramethylene group, a 1-methylpentamethylene group, a 2-methylpentamethylene group and a 3-methylpentamethylene group, in particular, an ethylene group is preferable.

k is an integer of usually 10 to 250, preferably 20 to 200, more preferably 40 to 150.

The polymer comprising a polyethylene glycol segment represented by the general formula [1], a monomer unit represented by the general formula [2] and a monomer unit represented by the general formula [3] as constituents (polymer relevant to the present invention), includes one represented by the general formula [6]:

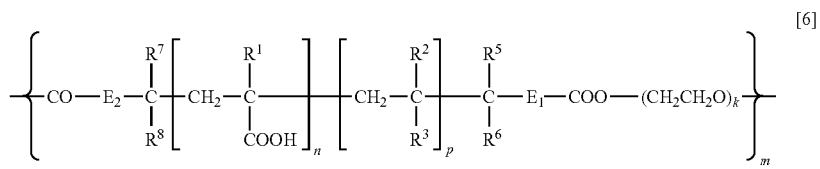

(wherein, R$^7$ represents a hydrogen atom or C$_1$-C$_3$ alkyl group, R$^8$ represents a cyano group or C$_1$-C$_3$ alkyl group, E$_2$ represents C$_1$-C$_6$ alkylene group, n represents an integer of 50-900, p represents an integer of 50-900, m represents an integer of 1-10, and R$^1$-R$^3$, R$^5$, R$^6$, E$_1$ and k are the same as described the above).

C$_1$-C$_3$ alkyl group represented by R$^7$ and R$^8$ in the general formula [6] may be straight chained or branched, and usually includes C$_1$-C$_3$ alkyl group, preferably C$_1$ alkyl group, which is specifically exemplified by, for example, a methyl group, an ethyl group a n-propyl group or an isopropyl group, in particular, a methyl group is preferable.

In particular, either of R$^7$ and R$^8$ is preferably a cyano group.

C$_1$-C$_6$ alkylene group represented by E$_2$ may be straight chained or branched, and includes usually C$_1$-C$_6$ alkylene group, preferably C$_1$-C$_4$ alkylene group, more preferably C$_2$ alkylene group, which is specifically exemplified by, for example, straight chain alkylene groups such as a methylene group, an ethylene group, a trimethylene group, a tetramethylene group, a pentamethylene group and a hexamethylene group; branched alkylene groups such as an ethylidene group, a propylene group, an isopropylidene group, an ethylethylene group, a 1-methyltrimethylene group, a 2-methyltrimethylene group, a 1-methyltetramethylene group, a 2-methyltetramethylene group, a 1-methylpentamethylene group, a 2-methylpentamethylene group and a 3-methylpentamethylene group, in particular, an ethylene group is preferable.

n and p are each independently an integer of usually 20 to 1,000, preferably 50 to 900, more preferably 75 to 600.

m is an integer of usually 1 to 10, preferably 2 to 6.

The weight average molecular weight of the polymer relevant to the present invention is usually 10,000 to 120,000, preferably 30,000 to 100,000.

Further, content of the polyethylene glycol segment represented by the general formula [1] in the polymer relevant to the present invention is usually 1-70% by weight, preferably 10-50% by weight.

Furthermore, content of the monomer unit represented by the general formula [2] and [3] in the polymer relevant to the present invention is usually 20-85% by weight, preferably 50-85% by weight, respectively.

1-2. Preparation Method

The polymer comprising the polyethylene glycol segment represented by the general formula [1], the monomer unit represented by the general formula [2] and the monomer unit represented by the general formula [3] as constituents (the polymer relevant to the present invention) can be obtained by copolymerizing, for example, in coexistence of an azo group-containing polyethylene glycol segment having a monomer unit represented by the general formula [10]:

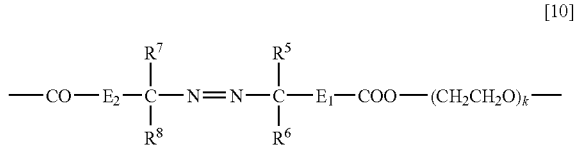

[10]

(wherein, $R^5$ to $R^8$, $E_1$, $E_2$ and k are the same as described the above), the compound represented by the general formula [11]:

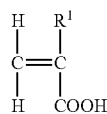

[11]

(wherein, $R^1$ is the same as described the above) and the compound represented by the general formula [12]:

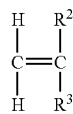

[12]

(wherein, $R^2$ and $R^3$ are the same as described the above).

Specific example of the compound represented by the general formula [11] includes, for example, acrylic acid or methacrylic acid.

Specific example of the compound represented by the general formula [12] includes, for example, methacrylic acid esters such as tert-butyl methacrylate, cyclohexyl methacrylate, 2-ethylhexyl methacrylate, dodecyl methacrylate, bornyl methacrylate, heptadecafluorooctylethyl methacrylate and 2,2,3,3,4,4,5,5-octafluoropentyl methacrylate; for example, α,β-unsaturated carboxylic acid esters such as cyclohexyl acrylate; for example, α,β-unsaturated carboxylic acid amides such as cyclohexyl methacrylamide; for example, vinyl ether such as cyclohexyl vinyl ether; α,β-unsaturated aliphatic hydrocarbons such as vinylcyclohexyl and allyl cyclohexyl; α,β-unsaturated aromatic hydrocarbons such as allyl benzene.

As the polyethylene glycol segment having the monomer unit represented by the general formula [10], the commercially available products or the appropriately synthesized products by a conventional method may be used. Specific example of commercially available product includes, for example, macro azo polymerization initiators such as VPE-0201, VPE-0401 and VPE-0601 (manufactured by Wako Pure Chemical Industries, Ltd.).

Also, specific example of the appropriately synthesized product by a conventional method, for example, may be easily produced according to the method of JP-A-4-372675. Namely, this product may be obtained by reacting polyethylene glycol represented by the general formula [13]:

$HO-(CH_2CH_2O)_k-OH$ [13]

(wherein, k is the same as described the above), with azo group-containing dibasic acid dihalide represented by the general formula [14]:

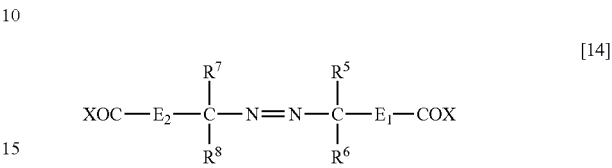

[14]

(wherein, X represents a halogen atom, and $R^5$ to $R^8$, $E_1$ and $E_2$ are the same as described the above) in the suitable solvent, if needed, in the presence of basic catalyst.

As azo group-containing polyethylene glycol segment having a monomer unit represented by the general formula [10], the product prepared according to the method described in, for example, JP-A-6-93100 or JP-A-6-322089 may be used. Namely, for example, a polyethylene glycol represented by the above general formula [13] reacts with azo group-containing dibasic acid represented by the general formula [15]:

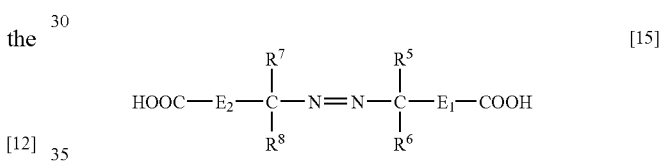

[15]

(wherein, $R^5$ to $R^8$, $E_1$ and $E_2$ are the same as described the above) in an appropriate solvent, if needed, in the existence of basic catalyst, using dehydrating agent to obtain the product.

In the general formula [14], the halogen atom represented by X includes, for example, fluorine atom, chlorine atom, bromine atom or iodine atom.

In the above preparation method, all the reaction is preferably carried out in existence of basic catalyst, specific example of available basic catalyst includes, for example, organic amines such as triethylamine, diisopropylethyl amine, N,N-dimethylaniline, piperidine, pyridine, 4-dimethylaminopyridine, 1,5-diazabicyclo[4.3.0]nona-5-ene, 1,8-diazabicyclo[5.4.0]undeca-7-ene, tri-n-butylamine and N-methylmorpholine; for example, metallic hydrides such as sodium hydride; and for example, basic alkaline metallic compounds such as n-butyllithium and tert-butyllithium.

Amount of basic catalyst to be used is not limited, but is appropriately selected from the range of, usually 0.5 to 5 times of mole, preferably, 0.5 to 1.5 times of mole, relative to the azo group-containing dibasic acid dihalide represented by the general formula [14], the azo group-containing dibasic acid represented by the general formula [15] or dehydrating agent.

Also, in the method of reacting said polyethylene glycol with an azo group-containing dibasic acid represented by the general formula [15], specific example of dehydrating agent to be used includes, but is not limited to, any type used as dehydrating condensing agent, for example, inorganic dehydrating agents such as concentrated sulfuric acid, diphosphorus pentaoxide and anhydrous zinc chloride; for example, carbodiimides such as dicyclohexylcarbodiimide, diisopropylcarbodiimide and 1-ethyl-3-(3-dimethylaminopropylcarbodiimide) hydrochloric acid salt; polyphosphoric acid, acetic anhydride, carbonyldiimidazole, or p-toluenesulfonyl chloride.

Amount of the dehydrating agent is not limited, but reaction rate becomes slow and final molecular weight is small when employing the smaller amount. On the other hand, when employing too much amount, high molecular weight can be obtained in a short time, but it is very difficult to control the molecular weight and it is uneconomical. Therefore, the amount is appropriately selected from the range of 1 to 5 times moles, preferably 2 to 3 times moles, relative to the azo group-containing dibasic acid.

In either of these methods, reaction solvents includes, for example, ethers such as diethyl ether, diisopropyl ether, tetrahydrofuran, dioxane and dimethoxyethane; for example, halogenated hydrocarbons such as carbon tetrachloride, chloroform, methylene chloride, dichloroethane and trichloroethylene; for example, hydrocarbons such as n-hexane, benzene, toluene and xylene; for example, esters such as ethyl acetate, butyl acetate and methyl propionate; acetonitrile, N,N-dimethylformamide or N,N-dimethylacetamide. These may be used alone or in combination with more than two solvents Ratio of use between the polyethylene glycol represented by the general formula [13], and the azo group-containing dibasic acid dihalide represented by the general formula [14] or the azo group-containing dibasic acid represented by the general formula [15] is not limited, and appropriately determined if needed. Use of each equal mole is preferable to obtain high molecular weight of the azo group-containing polyethylene glycol segment.

Reaction temperature is not limited, but too high temperature may allow the azo group to be decomposed, on the other hand, too low temperature may allow the reaction rate to be slow, and long time for preparation is needed, and it is difficult to obtain high molecular weight of azo group-containing polyethylene glycol segment. Therefore, usually, the reaction temperature is appropriately selected from the range of −10° C. to 60° C. Also, reaction temperature may be increased in stepwise from the low temperature.

Reaction time is different due to the preparation method, and usually, is selected appropriately from the range of 1 to 60 hours.

Isolation of the desired products can be carried out appropriately according to the types and amounts of the used raw material, basic catalyst, dehydrating agent or solvent, and the state of reaction solvent. When reaction solution is viscous, after diluting reaction solution with suitable solvents, and then the desired azo group-containing polyethylene glycol segment can be obtained by removing the impurities such as quaternary ammonium salt as the by-product, with operations such as filtration and water washing, and solvent. Also, said azo group-containing polyethylene glycol segment may be used to the next polymerization reaction without purification and/or isolation.

The polyethylene glycol represented by the above general formula [13], azo group-containing dibasic acid dihalide represented by the general formula [14], or azo group-containing dibasic acid represented by the general formula [15], to be used as raw material may be used as commercially available products, or may be produced appropriately by a conventional method.

The polymer relevant to the present invention, namely, the polymer comprising a polyethylene glycol segment having a group represented by the general formula [1], a monomer unit represented by the general formula [2] and a monomer unit represented by the general formula [3] as constituents, for example, can be obtained by polymerizing, in the hydrophilic organic solvent, the azo group-containing polyethylene glycol segment represented by the general formula [10], the compound represented by the general formula [11] and the compound represented by the general formula [12], with the selective setting of the amount of each use in order to obtain the desired level of composition ratio of polyethylene glycol segment, which is a main constituent unit of the resultant polymer, having the group represented by general formula [1], a monomer unit represented by general formula [2] and a monomer unit represented by general formula [3], and then by crystallizing and isolating from the resulting solution using insoluble organic solvent as precipitant.

The polymerization solvent includes, for example, ketones such as acetone and methyl ethyl ketone; alcohols such as methanol, ethanol, n-propanol and isopropanol; cyclic ethers such as tetrahydrofuran and 1,4-dioxane; hydrophilic organic solvents such as N-methylpyrrolidone, N,N'-dimethylacetamide and dimethylsulfoxide. These may be used alone or in combination with more than two other solvents, and also, a solvent containing water may be used within a range not influencing the reaction.

The above polymerization reaction method includes, for example, suspension polymerization, bulk polymerization or emulsion polymerization. In the polymerization reaction, azo group-containing polyethylene glycol segment and normal radical polymerization initiator (e.g. azobisisobutyronitrile, 2,2'-azobisisobutyric acid dimethyl ester, etc.) may be used at the same time.

In carrying out this copolymerization, a chain transfer agent (e.g. lauryl mercaptan, octyl mercaptan, butyl mercaptan, 2-mercaptoethanol, butyl thioglycolate, etc.) may be added to control the molecular weight.

The concentration in polymerization reaction is appropriately selected to control the total amount of said azo group containing polysiloxane segments, the compounds represented by the general formula [2] and [3] within the range of, usually 5 to 100% by weight (no solvent), preferably 5 to 80% by weight, more preferably 10 to 70% by weight, and further preferably 20 to 50% by weight.

Polymerization reaction is preferably carried out under inert gas atmosphere. Inert gas includes, for example, nitrogen gas or argon gas.

It becomes difficult to control the reaction when polymerization temperature is too high, and takes a long time for reaction according to the lowering of reaction rate when polymerization temperature is too low, and therefore, the polymerization temperature is usually 30 to 120° C., preferably 60 to 100° C. Also, the polymerization temperature may be changed to control the reaction according to the progress of polymerization reaction.

Polymerization time is usually 3 to 24 hours, preferably 5 to hours.

Organic solvent to be used as a precipitant is not limited, if precipitating the resulting polymer as insoluble matter, and includes, for example, hexane, ethyl acetate or diethyl ether. These may be used herein either singly or as appropriately combined. Further, when the amount of solvent to be used is too low, the amounts of residual polymerization solvent and the resultant un-reacted monomer increase, included in the obtained copolymer, and the amount of solvent is, usually more than two times of volume of polymerization solvent, preferably 3 to 20 times of volume, more preferably 5 to 10 times of volume.

Further, post treatments after polymerization reaction may be carried out according to the normal post-processing method in this art.

1-3. Property of Polymer

The polymer relevant to the present invention obtained in this way is expected for the application of, for example, resin composition such as resin compositions for paint and resin composition for coating; substrate materials for cosmetic such as substrate material for hair cosmetic (e.g. set agent, treatment agent, etc.) or substrate material for foundation; or mold releasing agent, coating agent, surface modifier or medical material, and in particular, is useful as the additive for measurement of cholesterol in a specific lipoprotein.

For example, polymer relevant to the present invention can protect a specific lipoprotein, and can inhibit the reaction of cholesterol in said specific lipoprotein by selecting the suitable monomer unit ratio constituting said polymer. By using this property, it is possible to measure cholesterol in a specific lipoprotein specifically, as described hereinafter.

In the present invention, "inhibition" means to retard (delay) or stop temporarily the reaction of cholesterol in protected specific lipoprotein.

Preferable specific example of polymer usable for this purpose includes, for example, the polymer essentially consisting of (i) to (iii) as described below (polymer (a) of the present invention).

(i) a polyethylene glycol segment having the group described in the general formula [1]:

(wherein, k is the same as the above-mentioned);

(ii) a monomer unit represented by the general formula [2]:

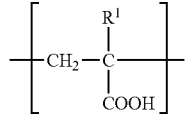

(wherein, $R^1$ is the same as the above-mentioned); and (iii) a third monomer unit selected from tert-butyl methacrylate, cyclohexyl methacrylate, 2-ethylhexyl methacrylate, dodecyl methacrylate, bornyl methacrylate, di(trifluoromethyl)methyl methacrylate, 2,2,3,3,4,4,5,5-octafluoropentyl methacrylate, heptadecafluorooctylethyl methacrylate, cyclohexyl methacrylamide, cyclohexyl acrylate, vinylcyclohexyl, arylcyclohexyl, cyclohexylvinyl ether and allylbenzene.

(1) HDL Protecting Polymer

For example, as the polymer protecting HDL, and inhibiting the reaction of cholesterol in HDL, one wherein a composition ratio (a weight ratio) of a monomer unit represented by the general formula [2] (monomer A) to a monomer unit represented by the general formula [3] (monomer B) is usually 2≦monomer B/monomer A, preferably 2≦monomer B/monomer A≦3, and a composition ratio (a weight ratio) of the total amounts (AB) of a monomer unit represented by the general formula [2] and a monomer unit represented by the general formula [3], relative to a polyethylene glycol segment (PEG) represented by the general formula [1] is usually 1≦AB/PEG≦10, preferably 2≦AB/PEG≦5.

Also, preferable example a polymer includes, for example, one having the monomer unit represented by the general formula [2] which is derived from acrylic acid or methacrylic acid, and the monomer unit represented by the general formula [3] containing as constituent one represented by the general formula [7]:

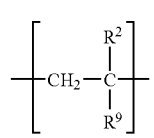

(wherein, $R^9$ represents $C_6$-$C_{12}$ alkyl group, an alkoxy group; $C_4$-$C_{16}$ alkoxycarbonyl group, a haloalkoxycarbonyl group, an alkylcarbamoyl group, an aralkyl group or a bornyloxycarbonyl group) is preferable.

In general formula [3], $C_6$-$C_{12}$ alkyl group represented by $R^9$ may be straight chained, branched or cyclic, which is specifically exemplified by, for example, the same as illustration in $C_6$-$C_{12}$ alkyl group represented by $R^3$ in the above general formula [3], in particular, for example, a cyclohexyl group or a cyclohexylmethyl group is preferable.

The alkoxy group represented by $R^9$ may be straight chained, branched or cyclic, and includes, usually $C_1$-$C_{10}$ alkoxy group, preferably $C_1$-$C_6$ alkoxy group, and specifically, for example, includes the same as illustration in the alkoxy group represented by $R^3$ in the above general formula [3], in particular, a cyclohexyloxy group is preferable.

The alkoxycarbonyl group represented by $R^9$ may be straight chained, branched or cyclic, which is specifically exemplified by, for example, a n-propoxycarbonyl group, an isopropoxycarbonyl group, a n-butoxycarbonyl group, an isobutoxycarbonyl group, a sec-butoxycarbonyl group, a tert-butoxycarbonyl group, a neobutoxycarbonyl group, a n-pentyloxycarbonyl group, an isopentyloxycarbonyl group, a sec-pentyloxycarbonyl group, a tert-pentyloxycarbonyl group, a neopentyloxycarbonyl group, a n-hexyloxycarbonyl group, an isohexyloxycarbonyl group, a sec-hexyloxycarbonyl group, a tert-hexyloxycarbonyl group, a neohexyloxycarbonyl group, a n-heptyloxycarbonyl group, an isoheptyloxycarbonyl group, a sec-heptyloxycarbonyl group, a tert-heptyloxycarbonyl group, a neoheptyloxycarbonyl group, a n-octyloxycarbonyl group, an isooctyloxycarbonyl group, a sec-octyloxycarbonyl group, a tert-octyloxycarbonyl group, a neooctyloxycarbonyl group, a 2-ethylhexyloxycarbonyl group, a n-nonyloxycarbonyl group, an isononyloxycarbonyl group, a sec-nonyloxycarbonyl group, a tert-nonyloxycarbonyl group, a neononyloxycarbonyl group, a n-decyloxycarbonyl group, an isodecyloxycarbonyl group, a sec-decyloxycarbonyl group, a tert-decyloxycarbonyl group, a neodecyloxycarbonyl group, a n-undecyloxycarbonyl group, an isoundecyloxycarbonyl group, a sec-undecyloxycarbonyl group, a tert-undecyloxycarbonyl group, a neoundecyloxycarbonyl group, a n-dodecyloxycarbonyl group, an isododecyloxycarbonyl group, a sec-dodecyloxycarbonyl group, a tert-dodecyloxycarbonyl group, a neododecyloxycarbonyl group, a n-tridecyloxycarbonyl group, an isotridecyloxycarbonyl group, a sec-tridecyloxycarbonyl group, a tert-tridecyloxycarbonyl group, a neotridecyloxycarbonyl group, a n-tetradecyloxycarbonyl group, an isotetradecyloxycarbonyl group, a sec-tetradecyloxycarbonyl group, a tert-tetradecyloxycarbonyl group, a neotetradecyloxycarbonyl group, a n-pentadecyloxycarbonyl group, an isopentadecyloxycarbonyl group, a sec-pentadecyloxycarbonyl group, a tert-pentadecyloxycarbonyl group, a neopentadecyloxycarbonyl group, a cyclohexyloxycarbonyl group, a cyclohexylmethoxycarbonyl group, a cycloheptyloxycarbonyl group, a cyclooctyloxycarbonyl group, a cyclononyloxycarbonyl group, a cyclodecyloxycarbonyl group, a cycloundecyloxycarbonyl group, a cyclododecyloxycarbonyl group, a cyclotridecyloxycarbonyl group, a cyclotetradecyloxycarbonyl group or a cyclopentadecyloxycarbonyl group, and in particular, for example, a tert-butoxycarbonyl group, a cyclohexyloxycarbonyl group, a 2-ethylhexyloxycarbonyl group or a dodecyloxycarbonyl group is preferable.

The haloalkoxycarbonyl group represented by $R^9$ may be straight chained, branched or cyclic, and includes, usually one wherein a part or all hydrogen atoms in $C_2$-$C_{13}$ alkoxycarbonyl group are substituted by a halogen atom (e.g. fluorine atom, bromine atom, chlorine atom, iodine atom, etc., and in particular, fluorine atom is preferable) and includes usually $C_2$-$C_{13}$ alkoxycarbonyl group, preferably $C_2$-$C_{11}$ alkoxycarbonyl group, which is specifically exemplified by, for example, a fluoromethoxycarbonyl group, a chloromethoxycarbonyl group, a bromomethoxycarbonyl group, a iodomethoxycarbonyl group, a trifluoromethoxycarbonyl group, a trichloromethoxycarbonyl group, a tribromomethoxycarbonyl group, a 2-fluoroethoxycarbonyl group, a 2-chloroethoxycarbonyl group, a 2-bromoethoxycarbonyl group, a 3-fluoropropoxycarbonyl group, a 3-chloropropoxycarbonyl group, a 3-bromopropoxycarbonyl group, a trifluoropropoxycarbonyl group, a trichloropropoxycarbonyl group, a tribromopropoxycarbonyl group a di(trifluoromethyl)methoxycarbonyl group, a di(trichloromethyl)methoxycarbonyl group, a di(tribromomethyl)methoxycarbonyl group, a heptafluoropropoxycarbonyl group, a heptachloropropoxycarbonyl group, a 4-fluorobutoxycarbonyl group, a 4-chlorobutoxycarbonyl group, a 4-bromobutoxycarbonyl group, a nonafluorobutoxycarbonyl group, a nonachlorobutoxycarbonyl group, a nonabromobutoxycarbonyl group, a 5-fluoropentyloxycarbonyl group, a 5-chloropentyloxycarbonyl group, a 5-bromopentyloxycarbonyl group, a 2,2,3,3,4,4,5,5-octafluoropentyloxycarbonyl group (—COOCH$_2$(CF$_2$)$_4$H), 2,2,3,3,4,4,5,5-octachloropentyloxycarbonyl group (—COOCH$_2$(CCl$_2$)$_4$H), a 2,2,3,3,4,4,5,5-octabromopentyloxycarbonyl group (—COOCH$_2$(CBr$_2$)$_4$H), a perfluoropentyloxycarbonyl group, a perchloropentyloxycarbonyl group, a perbromopentyloxycarbonyl group, a 6-fluorohexyloxycarbonyl group, a 6-chlorohexyloxycarbonyl group, a 6-bromohexyloxycarbonyl group, a perfluorohexyloxycarbonyl group, a perchlorohexyloxycarbonyl group, a perbromohexyloxycarbonyl group, a perfluoroheptyloxycarbonyl group, a perchloroheptyloxycarbonyl group, a perbromoheptyloxycarbonyl group, a perfluorooctyloxycarbonyl group, a perchlorooctyloxycarbonyl group, a perbromooctyloxycarbonyl group, a perfluorononyloxycarbonyl group, perchlorononyloxycarbonyl group, a perbromononyloxycarbonyl group, a heptadecafluorooctylethoxycarbonyl group (—COO(CH$_2$)$_2$(CF$_2$)$_7$CF$_3$), a heptadecachlorooctylethoxycarbonyl group (—COO(CH$_2$)$_2$(CCl$_2$)$_7$CCl$_3$), a heptadecabromooctylethoxycarbonyl group (—COO(CH$_2$)$_2$(CBr$_2$)$_7$CBr$_3$), a perfluorodecyloxycarbonyl group, a perchlorodecyloxycarbonyl group, a perbromodecyloxycarbonyl group, a perfluoroundecyloxycarbonyl group, a perchloroundecyloxycarbonyl group, a perbromoundecyloxycarbonyl group, a perfluorododecyloxycarbonyl group, a perchlorododecyloxycarbonyl group or a perbromododecyloxycarbonyl group, in particular, for example, a di(trifluoromethyl)methoxycarbonyl group, a 2,2,3,3,4,4,5,5-octafluoropentyloxycarbonyl group or a heptadecafluorooctylethoxycarbonyl group is preferable.

The alkylcarbamoyl group represented by $R^9$ may be straight chained, branched, or cyclic, and includes, usually $C_2$-$C_{11}$ alkylcarbamoyl group, preferably $C_2$-$C_7$ alkylcarbamoyl group, which is specifically exemplified by, for example, the same as illustration in alkylcarbamoyl group represented by $R^3$ in the above general formula [3], in particular, cyclohexylcarbamoyl group is preferable.

The aralkyl group represented by $R^9$ includes, usually $C_7$-$C_{12}$ aralkyl group, and specifically, for example, includes the same as illustration in the aralkyl group represented by $R^3$ in the general formula [3], in particular, a benzyl group is preferable.

Preferable specific example of the monomer unit represented by the general formula [7] includes, for example, one derived from tert-butyl methacrylate, dodecyl methacrylate, 2-ethylhexyl methacrylate, bornyl methacrylate, cyclohexyl methacrylate, cyclohexyl acrylate, di(trifluoromethyl)methyl methacrylate, heptadecafluorooctylethyl methacrylate, 2,2,3,3,4,4,5,5-octafluoropentyl methacrylate, cyclohexylmethacrylamide, cyclohexyl vinyl ether, vinylcyclohexyl, allylcyclohexyl or allylbenzene.

(2) LDL Protecting Polymer

For example, as the polymer protecting LDL, and inhibiting the reaction of cholesterol in LDL, one wherein a composition ratio (a weight ratio) of the monomer unit represented by the general formula [2] (monomer A) and the monomer unit represented by the general formula [3] (monomer B) is usually monomer B/monomer A$\leqq$1, preferably 0.5$\leqq$monomer B/monomer A$\leqq$1, and the composition ratio (a weight ratio) of the copolymer (AB) comprising the monomer unit represented by the general formula [2] and the monomer unit represented by the general formula [3], relative to the polyethylene glycol segment (PEG) represented by the general formula [1] is usually 1$\leqq$AB/PEG$\leqq$10, preferably 2$\leqq$AB/PEG$\leqq$5, is preferable.

Also, preferable examples a polymer include, for example, one having the monomer unit represented by the general formula [2] which is derived from acrylic acid or methacrylic acid, and the monomer unit represented by the general formula [3] containing as a constituent one represented by the general formula [8]:

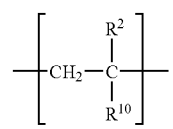

[8]

(wherein, $R^{10}$ represents $C_1$-$C_8$ alkoxycarbonyl group, and $R^2$ is the same as the above-mentioned), is preferable.

In general formula [8], the alkoxycarbonyl group represented by $R^{10}$ may be straight chained, branched or cyclic, and includes, usually $C_1$-$C_8$ alkoxycarbonyl group, which is specifically exemplified by, for example, a methoxycarbonyl group, an ethoxycarbonyl group, a n-propoxycarbonyl group, an isopropoxycarbonyl group, in particular, for example, a tert-butoxycarbonyl group or a cyclohexyloxycarbonyl group is preferable.

The alkyl group represented by $R^{10}$ may be straight chained, branched or cyclic, which is specifically exemplified by, for example the same as exemplified in $C_6$-$C_{12}$ alkyl group represented by $R^3$ in the general formula [3], and in particular, a cyclohexyl group is preferable.

The alkylcarbamoyl group represented by $R^{10}$ may be straight chained, branched, or cyclic, and includes usually $C_2$-$C_{11}$ alkylcarbamoyl group, preferably $C_2$-$C_7$ alkylcarbamoyl group, which is specifically exemplified by for example, the same as illustration in the alkylcarbamoyl group represented by $R^3$ in the above general formula [3], and in particular, cyclohexylcarbamoyl group is preferable.

Preferable specific example of the monomer unit represented in the general formula [8], for example, one derived from tert-butyl methacrylate, cyclohexyl methacrylate, cyclohexyl methacrylamide, cyclohexyl acrylate or vinylcyclohexyl, and in particular, for example, vinylcyclohexyl, tert-butyl methacrylate, cyclohexyl methacrylate or cyclohexyl metacrylamide is preferable.

(3) HDL·LDL Protecting Polymer

For example, as the polymer protecting LDL and HDL, and inhibiting the reaction of cholesterol in HDL and LDL, one wherein a composition ratio (a weight ratio) of the monomer unit represented by the general formula [2] (monomer A) and the monomer unit represented by the general formula [3] (monomer B) is usually 1<B/A<2, and a composition ratio (a weight ratio) (AB/C) of the copolymer (AB) comprising the monomer unit represented by the general formula [2] and the monomer unit represented by the general formula [3], relative to polyethylene glycol segment (PEG) represented by the general formula [1] is usually $1 \leq AB/C \leq 10$, preferably $2 \leq AB/C \leq 5$, is preferable.

Also, preferable examples of a polymer include, for example, one having the monomer unit represented by the general formula [2] which is derived from acrylic acid or methacrylic acid, and the monomer unit represented by the general formula [3] containing as constituent one represented by the general formula [9]

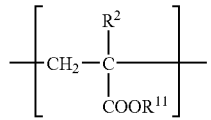

[9]

(wherein, $R^{11}$ represents $C_1$ to $C_6$ alkyl group, and $R^2$ is the same as the above-mentioned), is preferable.

$C_1$-$C_6$ alkyl group represented by $R^{11}$ in the general formula [9] may be any of straight chained, branched, or cyclic, which is specifically exemplified by, for example, the same as illustration in the alkyl group represented by $R^3$ in the above general formula [3], and in particular, for example, a tert-butyl group or a cyclohexyl group is preferable.

Preferable specific example of the monomer unit represented in the general formula [9], for example, includes one derived from tert-butyl methacrylate or cyclohexyl methacrylate, in particular, one derived from cyclohexyl methacrylate is preferable.

2. A Method for Determining Cholesterol in the Lipoprotein of the Present Invention The method for determining cholesterol in the lipoprotein of the present invention may determine the cholesterol in the specified lipoprotein in a biological sample in the presence of the polymer relevant to the present invention as described above (hereinafter, optionally may be abbreviated said polymer as simply "a polymer").

The method for determining cholesterol in the specified lipoprotein in a biological sample includes, in principle, the methods comprising decomposing the cholesterol in the biological sample into free cholesterol and fatty acid by the reaction with CHE, following by (a) determining hydrogen peroxide generated by reacting the free cholesterol with CO, or (b) determining NAD(P)H generated by reacting the free cholesterol with CHD and NAD(P).

More specifically, there can be exemplified by the method utilizing enzyme reactions, (1) an oxidative color producing method comprising decomposing cholesterol ester in a biological sample into free cholesterol and fatty acid by use of CHE; oxidizing this free cholesterol together with free cholesterol present from the beginning by use of CO to generate cholest-4-ene-3-one and hydrogen peroxide; then carrying out an oxidative color producing reaction of an oxidizable coloring reagent (e.g. combination of a coupler and a developer, or a color producing agent capable of producing color by itself on oxidation) with the generated hydrogen peroxide in the presence of POD; and determining the generated oxidized pigment calorimetrically; and (2) for example, an ultraviolet measuring method comprising decomposing cholesterol in a biological sample into free cholesterol and fatty acid by use of CHE; and reacting this free cholesterol together with free cholesterol present from the beginning with NAD (P) in the presence of CHD; and then determining the generated NAD(P)H by UV spectrometry at 340 nm.

That is, on the occasion of carrying out such methods, the determination method of the present invention may be carried out in the presence of (coexistent with) the polymer relevant to the present invention in the reaction system.

The method of the present invention may be carried out according to the method as described above except for the use of the polymer relevant to the present invention, and the reagents used in the above described method are also usable.

The method of the present invention is, in particular, divided roughly into the following 2 methods.

(1) A Method for Determining Cholesterol in the Lipoprotein Other than the Lipoprotein Protected by the Polymer Relevant to the Present Invention (Direct Method)

By contacting a biological sample with the polymer relevant to the present invention, the reaction of cholesterol in the specified lipoprotein in the aforementioned sample is inhibited, in other words, delayed or stopped temporarily; and the above described product generated by the reaction of the cholesterol in the lipoprotein other than the aforementioned specified lipoprotein is determined.

(2) A Method for Determining Cholesterol in the Lipoprotein Protected by the Polymer Relevant to the Present Invention (Elimination Method)

At first, by contacting a biological sample with the polymer relevant to the present invention, the reaction of cholesterol in the specified lipoprotein in the aforementioned sample is inhibited, in other words, delayed or stopped temporarily; as a result, the reaction of the cholesterol in the lipoprotein other than the specified lipoprotein is preceded preferentially and such cholesterol is eliminated (consumed) in advance; after that, the above described product generated by the reaction of cholesterol in the specified lipoprotein is determined.

2-1. Direct Method

The direct method as described above includes, for example, the following methods.

Direct Method (1)

In the presence (coexistence) of the polymer relevant to the present invention, the biological sample is reacted with CHE and CO to generate hydrogen peroxide; the generated hydrogen peroxide is reacted with POD and an oxidizable coloring reagent (e.g. combination with a coupler and a developer, a coloring reagent which develops color by itself by oxidation) to produce oxidized dye, and then the absorbance of the dye is measured; and based on the measurement value, the amount of cholesterol in the lipoprotein in the biological sample, namely, the amount of the cholesterol in the lipoprotein other than the specified lipoprotein, which the reaction is inhibited by contacting the biological sample with the polymer relevant to the present invention, is calculated.

Direct Method (2)

In the presence (coexistence) of the polymer relevant to the present invention, the biological sample is reacted with CHE, CHD and NAD(P) to generate NAD(P)H; and then the absorbance of the NAD(P)H is measured; and based on the measurement value, the amount of cholesterol in the lipoprotein in the biological sample, namely, the amount of the cholesterol in the lipoprotein other than the specified lipoprotein, which the reaction is inhibited by contacting the biological sample with the polymer relevant to the present invention, is calculated.

In the above direct method (1) and (2), the timing of measurement of the absorbance is the time (ODnb) when the reaction of the cholesterol in the lipoprotein, which is not inhibited by the polymer relevant to the present invention (the lipoprotein other than the specified lipoprotein which the reaction is inhibited by contacting the biological sample with the polymer relevant to the present invention), is substantially completed, and before the reaction of the cholesterol in the lipoprotein, which the reaction is inhibited by the polymer relevant to the present invention (the specified lipoprotein, which the reaction is inhibited by contacting the biological sample with the polymer relevant to the present invention), is substantially started. Since the timing of the measurement of the aforementioned absorbance may differ by the difference of determination method, the type and use concentration of the polymer relevant to the present invention, and the type and use concentration of other reagents such as enzymes, the appropriate timing of the measurement may be set, for example, by studying the reactivity (reaction curve) against each lipoprotein fraction.

In addition, in the above described direct method (1) and (2), the cholesterol in the lipoprotein other than the specified lipoprotein can be determined specifically by selecting and using the polymer relevant to the present invention properly. For example, (1) by using the polymer protecting HDL as described above, the amount of cholesterol in the lipoprotein other than HDL (the amount of LDL-cholesterol and VLDL-cholesterol) can be determined; (2) by using the polymer protecting LDL as described above, the amount of cholesterol in the lipoprotein other than LDL (the amount of HDL-cholesterol and VLDL-cholesterol) can be determined; (3) by using the polymer protecting HDL and LDL as described above, the amount of cholesterol in the lipoprotein other than HDL and LDL (the amount of VLDL-cholesterol) can be determined individually. The specific example of these polymers relevant to the present invention and the preferable embodiment are as described above.

2-2. Elimination Method

The elimination method as described above is further divided roughly into 2 methods as follows.

Elimination method (1): A method of measurement of the absorbance at 2 different time points, after contacting the biological sample with the polymer relevant to the present invention, is measured.

Elimination method (2): A method of elimination (consumption) of the cholesterol in the lipoprotein other than the lipoprotein protected by the polymer relevant to the present invention by leading it to an another reaction which does not affect the reaction of the cholesterol in the lipoprotein protected by the polymer relevant to the present invention.

(1) Elimination Method (1)

The elimination method as described above includes, for example, the following methods.

Elimination Method (1)-a

In the presence (coexistence) of the polymer relevant to the present invention, the biological sample is reacted with CHE and CO to generate hydrogen peroxide; the generated hydrogen peroxide is reacted with POD and an oxidizable coloring reagent (e.g. combination with a coupler and a developer, a coloring substance which develops color by itself by oxidation, etc.) to produce oxidized dye, and then the absorbance at 2 different time points are measured; and based on the measurement value, the amount of cholesterol in the lipoprotein in the biological sample, namely, the amount of the cholesterol in the specified lipoprotein, which the reaction is inhibited by contacting the biological sample with the polymer relevant to the present invention, is calculated.

Elimination Method (1)-b

In the presence (coexistence) of the polymer relevant to the present invention, the biological sample is reacted with CHE, CHD and NAD(P) to generate NAD(P)H; and then the absorbance at 2 different time points are measured; and based on the measurement value, the amount of cholesterol in the lipoprotein in the biological sample, namely, the amount of the cholesterol in the specified lipoprotein, which the reaction is inhibited by contacting the biological sample with the polymer relevant to the present invention, is calculated.

In the above elimination method (1)-a and (1)-b, the 2 different time points described are, (i) at the time (ODnb) when the reaction of the cholesterol in the lipoprotein, which the reaction is not inhibited by the polymer relevant to the present invention (the lipoprotein other than the specified lipoprotein, which the reaction is inhibited by contacting the biological sample with the polymer relevant to the present invention), is substantially completed, and before the reaction of the cholesterol in the lipoprotein, which the reaction is inhibited by the polymer relevant to the present invention (the specified lipoprotein which the reaction is inhibited by contacting the biological sample with the polymer relevant to the present invention), is substantially started, and (ii) at the time (ODt) when the reaction of the cholesterol in the lipoprotein, which the reaction is inhibited by the polymer relevant to the present invention (the specified lipoprotein, which the reaction is inhibited by contacting the biological sample with the polymer relevant to the present invention), is substantially completed. Since these 2 time points of measurement may differ by the difference of determination method, the type and use concentration of the polymer relevant to the present invention, and the type and use concentration of other reagents such as enzymes, the appropriate timing of the measurement may be set, for example, by studying the reactivity (reaction curve) against each lipoprotein fraction.

In addition, in the above elimination method (1)-a and (1)-b, the cholesterol in the specified lipoprotein can be determined specifically by selecting and using the polymer relevant to the present invention properly. For example, (1) by using the polymer protecting HDL as described above, the amount of HDL-cholesterol can be determined; (2) by using the polymer protecting LDL as described above, the amount of LDL-cholesterol can be determined; and (3) by using the polymer protecting HDL and LDL as described above, the amount of HDL-cholesterol and LDL-cholesterol can be determined. The specific example of these polymers involved in the present invention and the preferable embodiment are as described above.

In the above described elimination method (1)-a and (1)-b, (i) after the reaction of the cholesterol in the lipoprotein, which the reaction is not inhibited by the polymer relevant to the present invention (the lipoprotein other than the specified lipoprotein, which the reaction is inhibited by contacting the biological sample with the polymer relevant to the present invention), is substantially completed, preferably the reaction of the cholesterol in the lipoprotein, which the reaction is not inhibited by the polymer relevant to the present invention (the lipoprotein other than the specified lipoprotein, which the reaction is inhibited by contacting the biological sample with the polymer relevant to the present invention), is substantially completed, and after the time (ODnb) before the reaction of the cholesterol in the lipoprotein, which the reaction is inhibited by the polymer relevant to the present invention (the specified lipoprotein, which the reaction is inhibited by contacting the biological sample with the polymer relevant to the present invention), is substantially started, the coexistence of a substance that can release the protection of the polymer relevant to the present invention for the specified lipoprotein, in other words, a substance that can restore (regain) or stimulate the reaction of the cholesterol in the specified lipoprotein which is inhibited by the polymer relevant to the present invention in the reaction system is preferable. By this substance, the reaction of the cholesterol in the specified lipoprotein, which the reaction is inhibited by the polymer relevant to the present invention is restored (regained) or stimulated, and in consequence, the determination of the cholesterol in the objective specified lipoprotein can be completed (finished) within more short period of time.

In addition, by changing pH of the reaction system, after the reaction of the cholesterol in the lipoprotein, which the reaction is not inhibited by the polymer relevant to the present invention (the lipoprotein other than the specified lipoprotein, which the reaction is inhibited by contacting the biological sample with the polymer relevant to the present invention), is substantially completed, and after the time (ODnb) before the reaction of the cholesterol in the lipoprotein, which the reaction is inhibited by the polymer relevant to the present invention (the specified lipoprotein, which the reaction is inhibited by contacting the biological sample with the polymer relevant to the present invention), is substantially started, the protection of the polymer relevant to the present invention for the specified lipoprotein can also be released, in other words, the reaction of the specified lipoprotein which is inhibited by the polymer relevant to the present invention may also be restored (regained), or promoted by changing the pH of the reaction system.

(2) Elimination Method (2)

To practice the elimination method (2) of the present invention, in the presence of a reagent for eliminating the cholesterol in the lipoprotein other than the lipoprotein which is protected by the polymer relevant to the present invention, the cholesterol in the lipoprotein other than the lipoprotein protected by the polymer relevant to the present invention, is reacted with the aforementioned reagent, and the cholesterol in the lipoprotein other than the lipoprotein protected by the polymer relevant to the present invention, is eliminated (consumed) by leading it to an another reaction which does not affect the reaction of the cholesterol in the lipoprotein protected by the polymer relevant to the present invention, and after that, the reaction of the cholesterol in the specified lipoprotein, which is protected by the polymer relevant to the present invention, may be carried out.

For example, this kind of reagent for eliminating cholesterol in the lipoprotein other than the lipoprotein protected by the polymer relevant to the present invention, includes (i) a hydrogen peroxide-eliminating reagent for eliminating the hydrogen peroxide which is generated by the reaction of the cholesterol in a biological sample with CHE to decompose it to free cholesterol and fatty acid and by the reaction with CO, (ii) a NAD(P)H-eliminating reagent for eliminating NAD(P)H generated by the reaction of the cholesterol in a biological sample with CHE to decompose it to free cholesterol and fatty acid and by the reaction with CHD and NAD(P).

The hydrogen peroxide-eliminating reagent includes, for example, a combination of CHE, CO, POD and a coupler; a combination of CHE, CO, POD and a developer; a combination of CHE, CO, POD and a coupler and a developer; or a combination of CHE, CO and CAT. NAD(P)H-eliminating reagent includes a combination of CHE, CHD and NAD(P).

The elimination method (2) of the present invention using this kind of reagent for eliminating cholesterol in the lipoprotein other than the lipoprotein protected by the polymer relevant to the present invention, may be carried out, as follows.

Elimination Method (2)-a

In the presence (coexistence) of the polymer relevant to the present invention, the biological sample is reacted with CHE and CO to generate hydrogen peroxide; the generated hydrogen peroxide is reacted with POD and a coupler (or a developer) or CAT to eliminate (consume) the cholesterol in the lipoprotein other than the specified lipoprotein which the reaction is inhibited by contacting the biological sample with the polymer relevant to the present invention; and followed by the reaction with a developer (or a coupler), or a CAT inhibitor and an oxidizable coloring reagent to produce an oxidized dye; then the absorbance of the dye is measured; and based on the measurement value, the amount of cholesterol in the lipoprotein in the biological sample, namely, the amount of the cholesterol in the specified lipoprotein, which the reaction is inhibited by contacting the biological sample with the polymer relevant to the present invention, is calculated.

Elimination Method (2)-b

In the presence (coexistence) of the polymer relevant to the present invention, the biological sample is reacted with CHE, CHD and NAD(P) (or with CHE, CO, POD and a coupler and/or a developer) to lead the reaction to the reaction system which generates NAD(P)H (or hydrogen peroxide) by the reaction of the biological sample, the cholesterol in the lipoprotein other than the specified lipoprotein, which the reaction is inhibited by contacting the biological sample with the polymer relevant to the present invention, is eliminated (consumed); and followed by the reaction with CO, POD, an oxidizable coloring reagent and CHD inhibitor (or with CHD, NAD(P) and CO inhibitor) to produce an oxidized dye (or NAD(P)H); then the absorbance is measured; and based on the measurement value, the amount of cholesterol in the lipoprotein in the biological sample, namely, the amount of the cholesterol in the specified lipoprotein, which the reaction is inhibited by contacting the biological sample with the polymer relevant to the present invention, is calculated.

In the elimination method (2)-a and (2)-b, the amount of cholesterol in the specified lipoprotein in a biological sample can be determined by the measurement of absorbance at only single time point, namely, the time (ODb) when the reaction of the cholesterol in the lipoprotein, which the reaction is inhibited by the polymer relevant to the present invention (the specified lipoprotein which the reaction is inhibited by contacting the biological sample with the polymer relevant to the present invention), is substantially completed. However, in order to improve the measurement precision, it is preferable to measure absorbance at 2 different time points as same as described in the above elimination method (1)-a and (1)-b, namely, (i) at the time (ODbl) when the cholesterol in the lipoprotein other than the specified lipoprotein, which the reaction is inhibited by contacting the biological sample with the polymer relevant to the present invention, is substantially eliminated (consumed), and before the reaction of the cholesterol in the lipoprotein, which the reaction is inhibited by the polymer relevant to the present invention (the specified lipoprotein, which the reaction is inhibited by contacting the biological sample with the polymer relevant to the present invention), is substantially started, and (ii) the time (ODb) when the reaction of the cholesterol in the lipoprotein, which the reaction is inhibited by the polymer relevant to the present invention (the specified lipoprotein, which the reaction is inhibited by contacting the biological sample with the polymer relevant to the present invention), is substantially completed. As these 2 time points of measurement may differ by the difference of determination method, the type and use concentration of the polymer relevant to the present invention, and the type and use concentration of other reagents such as enzymes, therefore the measurement may be set accordingly, for example, by studying the reactivity (reaction curve) against each lipoprotein fraction.

In addition, in the above described elimination method (2)-a and (2)-b, the cholesterol in the specified lipoprotein can be determined specifically by selecting and using the polymer relevant to the present invention properly. For example, (1) by using the polymer protecting HDL as described above, the amount of HDL-cholesterol can be determined; (2) by using the polymer protecting LDL as described above, the amount of LDL-cholesterol can be determined; and (3) by using the polymer protecting HDL and LDL as described above, the amount of HDL-cholesterol and LDL-cholesterol can be determined. The specific example of these polymers involved in the present invention and the preferable embodiment are as described above.

In the above described elimination method (2)-a and (2)-b, after the time when the cholesterol in the lipoprotein other than the specified lipoprotein, which the reaction is inhibited by contacting the biological sample with the polymer relevant to the present invention, is substantially eliminated (consumed), preferably after the time when the cholesterol in the lipoprotein other than the specified lipoprotein, which the reaction is inhibited by contacting the biological sample with the polymer relevant to the present invention, is substantially eliminated (consumed), and before (ODbl) the cholesterol in the lipoprotein, which the reaction is inhibited by the employed polymer relevant to the present invention (the specified lipoprotein, which the reaction is inhibited by contacting the biological sample with the polymer relevant to the present invention), is substantially started. It is preferable to make a substance which can release the protection of the polymer relevant to the present invention for the specified lipoprotein, in other words, a substance which can restore (regain) or stimulate the reaction of the cholesterol in the specified lipoprotein inhibited by the polymer relevant to the present invention, to co-exist in the reaction system. By this substance, the reaction of the specified lipoprotein which is inhibited is restored (regained) or stimulated, and in consequence, the determination can be completed (finished) within more short period of time.

In addition, by changing the pH of the reaction system, after the cholesterol in the lipoprotein other than the specified lipoprotein, which the reaction is inhibited by contacting the biological sample with the polymer relevant to the present invention, is substantially eliminated (consumed), and after the time (ODbl) before the cholesterol in the lipoprotein, which the reaction is inhibited by the employed polymer relevant to the present invention (the specified lipoprotein, which the reaction is inhibited by contacting the biological sample with the polymer relevant to the present invention), is substantially started, the protection of the polymer relevant to the present invention for the specified lipoprotein can also be released, in other words, the reaction of the specified lipoprotein which is inhibited by the polymer relevant to the present invention may also be restored (regained), or promoted.

2-3. Specific Determination Method (1) Direct Method [Direct Method (1) and (2)]

The direct method [Direct method (1) and (2)] of the present invention may be any one of a single reagent solution method, a two reagent solution method or a method using more reagent solutions, and in the method using 2 or more reagent solutions, the polymer relevant to the present invention may be contained in a reagent solution which is mixed directly with the biological sample. In the case of a single reagent solution method, the polymer relevant to the present invention and all reagents for the cholesterol determination are contained in the aforementioned reagent solution.

The specific examples of the direct method [Direct method (1) and (2)] of the present invention will be shown below, but the method of the present invention is not limited thereto.

When the single reagent solution method is used, for example, the procedure is as described below:

The biological sample is mixed with a reagent solution comprising (1) the polymer relevant to the present invention, (2) CHE, (3) CO, POD and an oxidizable coloring reagent [or (3) CHD and NAD(P)] and (4) aqueous medium; then the absorbance (ODnb) is measured; and based on the absorbance, the amount of cholesterol in the specified lipoprotein in the biological sample (the amount of cholesterol in the lipoprotein other than the specified lipoprotein, which the reaction is inhibited by contacting the biological sample with the polymer relevant to the present invention) may be calculated.

When the 2 reagent solution method is used, for example, the procedure is as described below:

A biological sample is mixed with the first reagent solution comprising (1) the polymer relevant to the present invention and (2) aqueous medium; and then if needed, the absorbance (ODbl) is measured; and then the aforementioned mixed solution is mixed with the second reagent solution comprising (3) CHE, (4) CO [or (4) CHD] and (5) aqueous medium; and subsequently, the absorbance (ODnb) is measured; and based on this absorbance, the amount of cholesterol in the specified lipoprotein in the biological sample (the amount of cholesterol in the lipoprotein other than the specified lipoprotein, which the reaction is inhibited by contacting the biological sample with the polymer relevant to the present invention) may be calculated. When CO is contained in the second reagent solution, each POD, a coupler and a developer is contained in at least one of the first or the second reagent solution; and when CHD is contained in the second reagent solution, NAD(P) is contained in at least one of the first or the second reagent solution.

In the above described method, since the time point of the measurement of ODnb may differ by the difference of determination method, type and use concentration of the polymer relevant to the present invention, and the type and use concentration of other reagents such as enzymes, the appropriate timing of the measurement may be set accordingly, for example, by studying the reactivity (reaction curve) against each lipoprotein fraction.

In addition, in the above described single reagent solution method, the reaction condition between the biological sample and the reagent solution may differ by the type and use concentration of the polymer relevant to the present invention, and the type and use concentration of other reagents such as enzymes and the like, and therefore it cannot be said flatly. However, the condition may be set appropriately for the reaction temperature from the range of normally 15-40° C., preferably 25-40° C. and more preferably 30-40° C. and for the reaction time from the rage of 1-20 minutes, preferably 2-15 minutes and more preferably 3-10 minutes, for example, by studying the reactivity (reaction curve) against each lipoprotein fraction. In addition, the pH at the time of the reaction may also be set appropriately from the range of normally pH 5-11, preferably pH 5-10, more preferably pH 5.5-8.5, yet preferably pH 6-8 and particularly preferable pH range of around 7.

In the above described 2 reagent solution method, the reaction condition between the biological sample and the first reagent solution may differ by the type and use concentration of the polymer relevant to the present invention, and the type and use concentration of other reagents such as enzymes, and therefore it cannot be said flatly. However, the condition may be set appropriately for the reaction temperature from the range of normally 15-40° C., preferably 25-40° C. and more preferably 30-40° C. and for the reaction time from the rage of 1-20 minutes, preferably 2-15 minutes and more preferably 3-10 minutes, for example, by studying the reactivity (reaction curve) against each lipoprotein fraction. In addition, the pH at the time of the reaction may also be set appropriately from the range of normally pH 5-11, preferably pH 5-10, more preferably pH 5.5-8.5, yet preferably pH 6-8 and particularly preferable pH range of around 7. In addition, the reaction condition between the mixed solution of the biological sample and the first reagent solution and the second reagent solution is also in the same situation as above, and the condition may be set appropriately for the reaction temperature from the range of normally 15-40° C., preferably 25-40° C. and more preferably 30-40° C. and for the reaction time from the rage of 1-20 minutes, preferably 2-15 minutes and more preferably 3-10 minutes, for example, by studying the reactivity (reaction curve) against each lipoprotein fraction. In addition, the pH at the time of the reaction may also be set appropriately from the range of normally pH 5-11, preferably pH 5-10, more preferably pH 5.5-8.5, yet preferably pH 6-8 and particularly preferable pH range of around 7.

(2) Elimination Method (1) [Elimination Method (1)-a and (1)-b]

The elimination method (1) [Elimination method (1)-a and (1)-b] of the present invention may be any one of a single reagent solution method, a 2 reagent solution method or a method using more reagent solutions. In the method using 2 or more reagent solutions, the polymer relevant to the present invention may be contained in the reagent which is mixed directly with the biological sample, and when a substance which can release the protection of the polymer relevant to the present invention for the specified lipoprotein is used, the aforementioned substance may be contained in a reagent solution (e.g. the second reagent solution in the case of 2 reagent solution method) which is added at the time after the reaction of the cholesterol in the lipoprotein, which the reaction is not inhibited by the polymer relevant to the present invention (the lipoprotein other than the specified lipoprotein, which the reaction is inhibited by contacting the biological sample with the polymer relevant to the present invention), is substantially completed. In the case of single reagent solution method, it goes without saying that the polymer relevant to the present invention and all reagents for the cholesterol measurement is contained in the aforementioned reagent solution.

The specific examples of the elimination method (1) [Elimination method (1)-a and (1)-b] of the present invention will be shown below, but the method of the present invention is not limited thereto.

When the single reagent solution method is used, for example, the procedure is as described below:

The biological sample is mixed with a reagent solution comprising (1) the polymer relevant to the present invention, (2) CHE, (3) CO, POD and an oxidizable coloring reagent [or (3) CHD and NAD(P)] and (4) aqueous medium; the absorbance (ODnb) is measured at the time when the reaction of cholesterol in the lipoprotein, which the reaction is not inhibited by the polymer relevant to the present invention (the lipoprotein other than the specified lipoprotein, which the reaction is inhibited by contacting the biological sample with the polymer relevant to the present invention), is substantially completed, and before the reaction of the cholesterol in the lipoprotein, which the reaction is inhibited by the polymer relevant to the present invention (the specified lipoprotein, which the reaction is inhibited by contacting the biological sample with the polymer relevant to the present invention), is substantially started; and then the absorbance (ODt) is measured again at the time when the reaction of the cholesterol in the lipoprotein, which the reaction is inhibited by the polymer relevant to the present invention (the specified lipoprotein, which the reaction is inhibited by contacting the biological sample with the polymer relevant to the present invention), is substantially completed; and based on these absorbance, the amount of the cholesterol in the specified lipoprotein in the biological sample (the amount of the cholesterol in the specified lipoprotein, which the reaction is inhibited by contacting the biological sample with the polymer relevant to the present invention) may be calculated.

When the 2 reagent solution method is used, for example, the procedure is as described below:

The biological sample is mixed with the first reagent solution comprising (1) the polymer relevant to the present invention and (2) aqueous medium; and then if needed, the absorbance (ODbl) is measured; and then the aforementioned mixed solution is mixed with the second reagent solution comprising (3) CHE, (4) CO [or (4) CHD] and (5) aqueous medium; subsequently the absorbance (ODnb) is measured at the time the reaction of cholesterol in the lipoprotein, which the reaction is not inhibited by the polymer relevant to the present invention (the lipoprotein other than the specified lipoprotein, which the reaction is inhibited by contacting the biological sample with the polymer relevant to the present invention), is substantially completed, and before the reaction of the cholesterol in the lipoprotein, which the reaction is inhibited by the polymer relevant to the present invention (the specified lipoprotein, which the reaction is inhibited by contacting the biological sample with the polymer relevant to the present invention), is substantially started; and then the absorbance (ODt) is measured again at the time when the reaction of the cholesterol in the lipoprotein, which the reaction is inhibited by the polymer relevant to the present invention (the specified lipoprotein, which the reaction is inhibited by contacting the biological sample with the polymer relevant to the present invention), is substantially completed; and based on these absorbances, the amount of the cholesterol in the specified lipoprotein in the biological sample (the amount of cholesterol in the specified lipoprotein, which the reaction is inhibited by contacting the biological sample with the polymer relevant to the present invention) may be calculated. When CO is contained in the second reagent solution, each POD, a coupler and a developer is contained in at least one of the first or the second reagent solution; and when CHD is contained in the second reagent solution, NAD(P) is contained in at least one of the first or the second reagent solution.

In addition, for example, the present invention may also be carried out by the procedure as described below:

The biological sample is mixed with the first reagent solution comprising (1) the polymer relevant to the present invention, (2) CHE, (3) CO, POD and an oxidizable coloring reagent [or (3) CHD and NAD(P)] and (4) aqueous medium, then the absorbance (ODnb) is measured; the aforementioned mixed solution is mixed with the second reagent solution comprising (4) a substance which can release the protection of the polymer relevant to the present invention for the specified lipoprotein and (5) aqueous medium, and then the absorbance (ODt) is measured; and based on these absorbance, the amount of cholesterol in the specified lipoprotein in the biological sample (the amount of cholesterol in the specified lipoprotein, which the reaction is inhibited by contacting the biological sample with the polymer relevant to the present invention) may be calculated.

In the above described method, the time point of the measurement of ODnb and ODt may differ by the difference of determination method, type and use concentration of the polymer relevant to the present invention, and the type and use concentration of other reagents such as enzymes, and therefore the measurement may be set accordingly, for example, by studying the reactivity (reaction curve) against each lipoprotein fraction.

In addition, in the above described single reagent solution method, the reaction condition between the biological sample and the reagent solution may differ by the type and use concentration of the polymer relevant to the present invention, and the type and use concentration of other reagents such as enzymes, and therefore it cannot be said flatly. However, the condition may be set appropriately for the reaction temperature from the range of normally 15-40° C., preferably 25-40° C. and more preferably 30-40° C. and for the reaction time from the rage of 1-20 minutes, preferably 2-15 minutes and more preferably 3-10 minutes, for example, by studying the reactivity (reaction curve) against each lipoprotein fraction. In addition, the pH at the time of the reaction may also be set appropriately from the range of normally pH 5-11, preferably pH 5-10, more preferably pH 5.5-8.5, yet preferably pH 6-8 and particularly preferable pH range of around 7.

In the above described 2 reagent solution method, the reaction condition between the biological sample and the first reagent solution may differ by the type and use concentration of the polymer relevant to the present invention, and the type and use concentration of other reagents such as enzymes, and therefore it cannot be said flatly. However, the condition may be set appropriately for the reaction temperature from the range of normally 15-40° C., preferably 25-40° C. and more preferably 30-40° C. and for the reaction time from the rage of 1-20 minutes, preferably 2-15 minutes and more preferably 3-10 minutes, for example, by studying the reactivity (reaction curve) against each lipoprotein fraction. In addition, the pH at the time of the reaction may also be set appropriately from the range of normally pH 5-11, preferably pH 5-10, more preferably pH 5.5-8.5, yet preferably pH 6-8 and particularly preferable pH range of around 7. In addition, the reaction condition between the mixed solution of the biological sample with the first reagent solution, and the second reagent solution is also in the same situation as described above, and the condition may be set appropriately for the reaction temperature from the range of normally 15-40° C., preferably 25-40° C. and more preferably 30-40° C. and for the reaction time from the rage of 1-20 minutes, preferably 2-15 minutes and more preferably 3-10 minutes, for example, by studying the reactivity (reaction curve) against each lipoprotein fraction. In addition, the pH at the time of the reaction may also be set appropriately from the range of normally pH 5-11, preferably pH 5-10, more preferably pH 5.5-8.5, yet preferably pH 6-8 and particularly preferable pH range of around 7.

(3) Elimination Method (2) [Elimination Method (2)-a and (2)-b]

The elimination method (2) [Elimination method (2)-a and (2)-b] of the present invention may be carried out by the method normally using 2 or more reagent solutions. In the method using 2 or more reagent solutions, the polymer relevant to the present invention may be contained in a reagent solution which is mixed directly with the biological sample. In addition, in the above described elimination method (2)-a, POD and a coupler, POD and a developer, or CAT may be contained in a reagent solution which is added at the time before the reaction of the cholesterol in the lipoprotein, which the reaction is inhibited by the polymer relevant to the present invention (the specified lipoprotein, which the reaction is inhibited by contacting the biological sample with the polymer relevant to the present invention), is substantially started; in the above described elimination method (2)-b, POD and a coupler and/or a developer, or NAD(P) may be contained in a reagent solution which is added at the time before the reaction of the cholesterol in the lipoprotein, which the reaction is inhibited by the polymer relevant to the present invention (the specified lipoprotein, which the reaction is inhibited by contacting the biological sample with the polymer relevant to the present invention), is substantially started. When a substance which can release the protection of the polymer relevant to the present invention for the specified lipoprotein is used, the aforementioned substance may be contained in a reagent solution (e.g. the second reagent solution in the case of 2 reagent solution method), which is added at the time after the cholesterol in the lipoprotein, which the reaction is not inhibited by the polymer relevant to the present invention (the lipoprotein other than the specified lipoprotein, which the reaction is inhibited by contacting the biological sample with the polymer relevant to the present invention), is substantially eliminated (consumed).

The specific examples of the elimination method (2) [Elimination method (2)-a and (2)-b] of the present invention will be shown below, but the method of the present invention is not limited thereto.

For example, the elimination method (2)-a may be carried out by the procedure as described below:

The biological sample is mixed with the first reagent solution comprising (1) the polymer relevant to the present invention, (2) CHE, (3) CO, (4) POD and a coupler (or a developer) [or (4) CAT] and (5) aqueous medium; then if needed, the absorbance (ODbl) is measured; and then the aforementioned mixed solution is mixed with the second reagent solution comprising (6) a developer (or a coupler) [or (6) CAT inhibitor], (7) aqueous medium, and if needed, (8) a substance which can release the protection of the polymer relevant to the present invention for the specified lipoprotein, and then the absorbance (ODb) is measured; and based on these absorbance, the amount of cholesterol in the specified lipoprotein in the biological sample (the amount of cholesterol in the lipoprotein other than the specified lipoprotein, which the reaction is inhibited by contacting the biological sample with the polymer relevant to the present invention) may be calculated. When CAT is contained in the first reagent solution, each POD, a coupler and a developer is contained in at least one of the first or the second reagent solution. In addition, CHE, CO and POD may be contained in both the first and the second reagent solution.

For example, the elimination method (2)-b may be carried out by the procedure as described below:

The biological sample is mixed with the first reagent solution comprising (1) the polymer relevant to the present invention, (2) CHE, (3) CO, POD and a coupler and/or a developer

[or (3) CHD and NAD(P)] and (5) aqueous medium; then if needed, the absorbance (ODbl) is measured; and then the aforementioned mixed solution is mixed with the second reagent solution comprising (6) CHD, NAD(P) and CO inhibitor [or (6) CO, POD, an oxidizable coloring reagent and CHD inhibitor], and (7) aqueous medium, and if needed, (8) a substance which can release the protection of the polymer relevant to the present invention for the specified lipoprotein, and then the absorbance (ODb) is measured; and based on these absorbance, the amount of cholesterol in the specified lipoprotein in the biological sample (the amount of cholesterol in the lipoprotein other than the specified lipoprotein, which the reaction is inhibited by contacting the biological sample with the polymer relevant to the present invention) may be calculated.

In the above described method, as the time point of the measurement of ODb may differ by the difference of determination method, the type and use concentration of the polymer relevant to the present invention, and the type and use concentration of other reagents such as enzymes, and therefore the measurement may be set accordingly, for example, by studying the reactivity (reaction curve) against each lipoprotein fraction.

In the above described method, the reaction condition between the biological sample and the first reagent solution may differ by the type and use concentration of the polymer relevant to the present invention, and the type and use concentration of other reagents such as enzymes, and therefore it cannot be said flatly. However, the condition may be set appropriately for the reaction temperature from the range of normally 15-40° C., preferably 25-40° C. and more preferably 30-40° C. and for the reaction time from the rage of 1-20 minutes, preferably 2-15 minutes and more preferably 3-10 minutes, for example, by studying the reactivity (reaction curve) against each lipoprotein fraction. In addition, the pH at the time of the reaction may also be set appropriately from the range of normally pH 5-11, preferably pH 5-10, more preferably pH 5.5-8.5, yet preferably pH 6-8 and particularly preferable pH range of around 7. In addition, the reaction condition between the mixed solution of the biological sample with the first reagent solution and the second reagent solution is also in the same situation as described above, and the condition may be set appropriately for the reaction temperature from the range of normally 15-40° C., preferably 25-40° C. and more preferably 30-40° C. and for the reaction time from the rage of 1-20 minutes, preferably 2-15 minutes and more preferably 3-10 minutes, for example, by studying the reactivity (reaction curve) against each lipoprotein fraction. Furthermore, the pH at the time of the reaction may also be set appropriately from the range of normally pH 5-11, preferably pH 5-10, more preferably pH 5.5-8.5, yet preferably pH 6-8 and particularly preferable pH range of around 7.

(4) Calculation of the Amount of Cholesterol in the Lipoprotein

In the method of the present invention as described above, a calculation of the amount of cholesterol in the lipoprotein in the biological sample based on the measured absorbance may be performed, for example, by the procedure as described below:

Direct Method [Direct Method (1) and (2)]
(1) ODnb is calculated in advance by the same way as described above using as a sample a standard preparation such as, for example, standard solution comprising known concentration of the cholesterol in the aforementioned lipoprotein other than the specified lipoprotein (the cholesterol in the lipoprotein other than the specified lipoprotein, which the reaction is inhibited by contacting with the polymer relevant to the present invention) and then the value of the amount of cholesterol in the lipoprotein other than the specified lipoprotein in the biological sample (the cholesterol in the lipoprotein other than the specified lipoprotein, which the reaction is inhibited by contacting the biological sample with the polymer relevant to the present invention) may be calculated by fitting the ODnb to a standard curve showing the relationship between the concentration of cholesterol in the lipoprotein other than the specified lipoprotein.

(2) The absorbance (ODtv) is obtained by subtracting ODbl [or the value derived from ODbl (e.g. the value obtained by multiplying ODbl by the volume correction coefficient)] from ODnb; and then, by fitting the obtained absorbance (ODtv) to a standard curve showing the relationship between the concentration of cholesterol in the lipoprotein other than the specified lipoprotein and ODtv, which is prepared in advance by the same way as described above using a standard preparation such as, for example, standard solution comprising known concentration of the cholesterol in the aforementioned lipoprotein other than the specified lipoprotein (the cholesterol in the lipoprotein other than the specified lipoprotein, which the reaction is inhibited by contacting with the polymer relevant to the present invention) as a sample, the value of the amount of cholesterol in the lipoprotein other than the specified lipoprotein in the biological sample (the cholesterol in the lipoprotein other than the specified lipoprotein, which the reaction is inhibited by contacting the biological sample with the polymer relevant to the present invention) may be calculated.

Elimination Method (1) [Direct Method (1)-a and (1)-b]
(1) The absorbance (ODcb) is obtained by subtracting ODnb [or the value derived from ODnb (for example, the value obtained by multiplying ODnb by the volume correction coefficient)] from ODt, and then, by fitting the obtained absorbance (ODcb) to a standard curve showing the relationship between the concentration of cholesterol in the specified lipoprotein and ODcb, which is prepared in advance by the same way as described above using a standard preparation such as, for example, standard solution comprising known concentration of the cholesterol in the aforementioned specified lipoprotein (the cholesterol in the specified lipoprotein, which the reaction is inhibited by contacting with the polymer relevant to the present invention) as a sample, the value of the amount of cholesterol in the specified lipoprotein in the biological sample (the cholesterol in the specified lipoprotein, which the reaction is inhibited by contacting the biological sample with the polymer relevant to the present invention) may be calculated.

(2) The absorbance (ODcnb) is obtained by subtracting ODbl [or the value derived from ODbl (for example, the value obtained by multiplying ODbl by the volume correction coefficient)] from ODnb; and the absorbance (ODct) is obtained by subtracting ODbl [or the value derived from ODbl (for example, the value obtained by multiplying ODbl by the volume correction coefficient)] from ODt; and further the absorbance (ODcb) is obtained by subtracting ODcnb from ODct. By fitting the obtained absorbance (ODcb) to a standard curve showing the relationship between the concentration of cholesterol in the specified lipoprotein and ODcb, which is prepared in advance by the same way as described above using a standard preparation such as, for example, standard solution comprising known concentration of the cholesterol in the aforementioned specified lipoprotein (the cholesterol in the specified lipoprotein, which the reaction is inhibited by contacting with the polymer relevant to the present invention) as a sample, the value of the amount of cholesterol in the specified lipoprotein in the biological sample (the cholesterol in the specified lipoprotein, which the reaction is inhibited by contacting the biological sample with the polymer relevant to the present invention) may be calculated.

Elimination Method (2) [Direct Method (2)-a and (2)-b]

(1) By fitting the absorbance (ODb) to a standard curve showing the relationship between the concentration of cholesterol in the specified lipoprotein and ODb, which is prepared in advance by the same way as described above using a standard preparation such as, for example, standard solution comprising known concentration of the cholesterol in the aforementioned specified lipoprotein (the cholesterol in the specified lipoprotein, which the reaction is inhibited by contacting with the polymer relevant to the present invention) as a sample, the value of the amount of cholesterol in the specified lipoprotein in the biological sample (the cholesterol in the specified lipoprotein, which the reaction is inhibited by contacting the biological sample with the polymer relevant to the present invention) may be calculated.

(2) The absorbance (ODcb) is obtained by subtracting ODbl [or the value derived from ODbl (for example, the value obtained by multiplying ODbl by the volume correction coefficient)] from ODb, and then, by fitting the obtained absorbance (ODcb) to a standard curve showing the relationship between the concentration of cholesterol in the specified lipoprotein and ODcb, which is prepared in advance by the same way as described above using a standard preparation such as, for example, standard solution comprising known concentration of the cholesterol in the aforementioned specified lipoprotein (the cholesterol in the specified lipoprotein, which the reaction is inhibited by contacting with the polymer relevant to the present invention) as a sample, the value of the amount of cholesterol in the specified lipoprotein in the biological sample (the cholesterol in the specified lipoprotein, which the reaction is inhibited by contacting the biological sample with the polymer relevant to the present invention) may be calculated.

2-4 Aspect and Use Concentration of Each Constituent Element

Preferable aspect, specific example and use concentration of each constituent element of the present invention are described below.

(1) The Polymer Relevant to the Present Invention

Preferable aspect and specific example of the polymer of the present invention are as described above.

In addition, the use concentration of the polymer relevant to the present invention may be the concentration which can inhibit the reaction of cholesterol in the specified lipoprotein and precede the reaction of cholesterol in the lipoprotein other than the specified lipoprotein, and the concentration in a reagent solution which contact directly with the biological sample is normally 0.001-10% (w/v), preferably 0.05-2% (w/v). In addition, these polymers of the present invention may be used alone or in combination of 2 types or more appropriately.

(2) CO

The CO to be used in the present invention includes the ones usually used in this field, for example, the ones derived from microorganisms belonging to genus *Nocardia*, genus *Pseudomonas* and the like and the ones derived from animal organ such as the bovine pancreas. The use amount of the CO, for example, as the concentration of the CO in the first reagent solution in the 2 reagent solution method is normally 0.03-330 u/ml, preferably 0.07-130 u/ml and more preferably 0.13-65 u/ml, or as the concentration in the final reaction solution, normally 0.02-250 u/ml, preferably 0.05-100 u/ml and more preferably 0.1-50 u/ml.

In the case of single reagent solution method, the concentration of the CO is selected appropriately from the above described concentration rage of the final reaction solution. (Hereinafter, the same as described above.)

(3) CHE

The CHE to be used in the present invention includes the ones usually used in this field, for example, the ones derived from microorganisms belonging to genus *Candida*, genus *Pseudomonas* and the like and the ones derived from animal organ such as the bovine pancreas. The use amount of the CHE, for example, as the concentration of the CHE in the first reagent solution in the 2 reagent solution method, is normally 0.03-330, u/ml, preferably 0.07-130 u/ml and more preferably 0.13-65 u/ml, or as the concentration in the final reaction solution, normally 0.02-250 u/ml, preferably 0.05-100 u/ml and more preferably 0.1-50 u/ml.

(4) POD

The POD to be used in the present invention includes the ones usually used in this field, for example, the ones derived from plant such as horse radish, soy bean and radish, the ones derived from microorganisms such as fungi and yeast, and the ones derived from the white blood cell, the thyroid gland of animal and the like. The use amount of the POD, for example, as the concentration of the POD in the first reagent solution in the 2 reagent solution method, is normally 0.1-1000 u/ml, preferably 0.25-400 u/ml and more preferably 0.5-200 u/ml, or as the concentration in the final reaction solution, normally 0.1-250 u/ml, preferably 0.25-100 u/ml and more preferably 0.5-50 u/ml.

(5) Oxidized Coloring Reagent

Oxidized coloring reagent to be used in the present invention may be any of reagents coloring by the reaction with hydrogen peroxide in the presence of POD, and includes, for example, combination of couplers such as 4-aminoantipyrine (hereinafter abbreviated to 4-AA), and a developer resulting in dye by oxidative condensation with said coupler, i.e. for example, combination of 4-AA and phenolic compound, naphtholic compound or aniline type compound; combination of 3-methyl-2-benzothiazolinone hydrazone and aniline type compound; for example, color developer coloring by itself according to oxidation, such as 2,2'-azinobis(3-ethylbenzothiazoline-6-sulfonic acid), triphenylmethane type leuco dye, diphenylamine derivatives, benzidine derivatives, triarylimidazole derivatives, leucomethyleneblue derivatives or o-phenylenediamine derivatives.

Specific example of phenolic type compound as a developer includes, for example, phenol, p-chlorophenol or 2,4-dichlorophenol, and specific example of naphthol type compound includes, for example, 1-naphthol, 1-naphthol-2-sulfonic acid or 1-naphthol-2-carboxylic acid, and also, specific example of aniline type compound includes, for example, N,N-diethylaniline, N-ethyl-N-(β-hydroxyethyl)-m-toluidine, N-ethyl-N-(2-hydroxy-3-sulfopropyl)-3,5-dimethoxyaniline (DAOS), N-ethyl-N-(2-hydroxy-3-sulfopropyl)-3,5-dimethoxy-4-fluoroaniline (FDAOS), N-(2-hydroxy-3-sulfopropyl)-3,5-dimethoxyaniline (HDAOS), N-ethyl-N-(2-hydroxy-3-sulfopropyl)-m-toluidine (TOOS), N-ethyl-N-(3-methylphenyl)-N'-succinyl-ethylenediamine (EMSE) or N-(3-sulfopropyl)-3-methoxy-5-methylaniline (HMMPS).

When the combination of a coupler and a developer is used, amount of a coupler to be used depends on type and combination of a coupler to be used, for example, the coupler concentration contained in the first reagent solution by 2 reagent solution method is the range of, usually, 0.01 to 400 mM, preferably, 0.1 to 40 mM, more preferably, 0.2 to 10 mM, and the coupler concentration contained in final reaction solution is the range of usually, 0.01 to 100 mM, preferably, 0.1 to 10 mM. Also, amount of 4-AA to be used as a coupler, for example, as the coupler concentration contained in the first reagent solution by 2 reagent solution method is the range of, usually, 0.01 to 200 mM, preferably, 0.1 to 40 mM, more preferably, 0.2 to 10 mM, and the coupler concentration contained in final reaction solution is the range of usually, 0.01 to 50 mM, preferably, 0.1 to 5 mM.

Also, amount of a developer to be used depends on type and combination of a coupler to be used, therefore, it cannot be said flatly, but, for example, the developer concentration in the first reagent solution by 2 reagent solution method is the range of, usually, 0.01 to 200 mM, preferably, 0.1 to 40 mM, more preferably, 0.2 to 10 mM, and the developer concentration in the final reaction solution is the range of, usually, 0.01 to 50 mM, preferably, 0.1 to 5 mM.

Specific example of triphenylmethane type leuco dye includes, for example, leucomalachite green, bis(p-diethylaminophenyl)-2-sulfophenylmethane or bis(p-diethylaminophenyl)-3,4-disulfopropoxyphenylmethane disodium salt, and specific example of diphenylamine derivative includes, for example, bis[4-di(2-butoxyethyl)amino-2-methylphenyl] amine or N,N-bis(4-diethylamino-2-methylphenyl)-N'-p-toluenesulfonylurea, and also, specific example of leucomethylene blue derivative includes, for example, 10-(carboxymethylaminocarbonyl)-3,7-bis(dimethylamino) phenothiazine sodium salt or 10-[3-(methoxycarbonylaminomethyl) phenylmethylaminocarbony l]-3,7-bis(dimethylamino) phenothiazine, and further specific example of benzidine derivative includes, for example, benzidine, o-tolidine, o-dianisidine or 3,3'-diaminobenzidine, 3,3',5,5'-tetraminobenzidine and specific example of triarylimidazole derivative includes, for example, 2-(4-carboxyphenyl)-3-N-methylcarbamoyl-4,5-bis(4-diethylaminophenyl)imidazole or 2-(3-methoxy-4-diethylaminophenyl)-3-N-methylcarbamoyl-4, 5-bis(2-methyl-4-diethylaminophenyl)imidazole.

The use amount of these coloring reagents may be within the range of concentration to be usually used in this field.

(6) CAT

The CAT to be used in the present invention includes the ones to be usually used in this field, for example, the ones derived from animal organ such as the bovine liver, the ones derived from plant such as chloroplast and the ones derived from microorganisms belonging to genus *Micrococcus*, genus *Rhodopseudomonas* and the like. The use amount of the CAT, for example, as the concentration of the CAT in the first reagent solution in the 2 reagent solution method, is normally 10-50000 u/ml, preferably 100-5000 u/ml and more preferably 50-2000 u/ml.

(7) CHD

The CHD to be used in the present invention includes the ones usually used in this field, for example, the one derived from microorganism belonging to genus *Nocardia* and the like. The use amount of the CHD, for example, as the concentration of the CHD in the first reagent solution in the 2 reagent solution method, is normally 0.1-150 u/ml, preferably 0.3-100 u/ml and more preferably 0.5-60 u/ml; and the concentration in the final reaction solution is normally 0.1-100 u/ml and preferably 0.5-50 u/ml.

(8) NAD(P)

The NAD(P) to be used in the present invention includes the ones usually used in this field, for example, the one derived from yeast. The use amount of the NAD(P), for example, as the concentration of the NAD(P) in the first reagent solution in the 2 reagent solution method, is normally 0.2-70 mM, preferably 0.5-50 mM and more preferably 1-20 mM; and the concentration in the final reaction solution is normally 0.2-50 mM and preferably 1-10 mM.

(9) CAT Inhibitor

The CAT inhibitor to be used in the present invention includes the ones usually used in this field, for example, $NaN_3$ and 3-amino-1,2,4-triazole. The use amount of these CAT inhibitors may differ by the type of the CAT inhibitor to be used and cannot be said flatly, however, for example, the concentration of the CAT inhibitor in the second reagent solution in the 2 reagent solution method is normally 0.01-10% (w/v), preferably 0.02-5% (w/v) and more preferably 0.03-3% (w/v).

(10) CO Inhibitor

The CO inhibitor to be used in the present invention includes the ones usually used in this field, for example, $Ag^+$ ion, $Zn^{2+}$ ion and glutathione. The use amount of these CO inhibitors may differ by the type of the CO inhibitor to be used and cannot be said flatly, however, for example, the concentration of the CO inhibitor in the second reagent solution in the 2 reagent solution method is normally 0.00002-40% (w/v), preferably 0.0002-4% (w/v) and more preferably 0.002-0.4% (w/v).

(11) CHD Inhibitor

The CHD inhibitor to be used in the present invention includes the ones usually used in this field, for example, $Ag^+$ ion and $Zn^{2+}$ ion. The use amount of these CHD inhibitors may differ by the type of the CHD inhibitor to be used and cannot be said flatly, however, for example, the concentration of the CHD inhibitor in the second reagent solution in the 2 reagent solution method is normally 0.00001-70% (w/v), preferably 0.0001-7% (w/v) and more preferably 0.001-0.7% (w/v).

(12) Aqueous Medium

The aqueous medium to be used in the present invention includes water or buffer solution. The buffering agent composing a buffer solution may be the one having buffer action within the rage of pH 5-11 and having no inhibiting action against the reaction of the cholesterol assay, and includes the ones usually used in this field, for example Tris(hydroxymethyl)aminomethane, Good's buffering agent (PIPES, BES, TES or HEPES), phosphate, borate, imidazole. The use concentration is usually in the range of 1 mM to 2 M, preferably 10 mM to 1 M, and the pH is usually 5-11, preferably 5-10, more preferably 5.5-8.5, yet more preferably 6-8 and particularly preferable pH around 7.

In addition, when the protection of the polymer relevant to the present invention for the specified lipoprotein is released, in other words, the reactivity of the specified lipoprotein, which the reaction is inhibited by the polymer relevant to the present invention, is restored (regained) or stimulated, by changing the pH of the reaction system after the cholesterol in the lipoprotein other than the specified lipoprotein, which the reaction is inhibited by contacting the biological sample with the polymer relevant to the present invention, is substantially eliminated (consumed), and after the time (ODbl) before the cholesterol in the lipoprotein, which the reaction is inhibited by the employed polymer relevant to the present invention (the specified lipoprotein, which the reaction is inhibited by contacting the biological sample with the polymer relevant to the present invention), is substantially started, the pH of the reagent solution comprising the polymer relevant to the present invention, which is mixed directly with the biological sample (e.g. the first reagent solution), may be made higher or lower to the level, at which the protection of the polymer relevant to the present invention for the specified lipoprotein, can be released, than the pH of the reagent solution to be added at the time after the reaction of cholesterol in the lipoprotein, which the reaction is not inhibited by the polymer relevant to the present invention (the lipoprotein other than the specified lipoprotein, which the reaction is inhibited by contacting the biological sample with the polymer relevant to the present invention) is substantially completed (for example, the second reagent solution). The specific difference of pH between these reagent solutions may be different by the type and the concentration of the polymer of the present invention to be employed and cannot be said flatly, however, it is usually 0.5-3, preferably 1-3.

(13) The Substance which can Release the Protection of the Polymer Relevant to the Present Invention for the Specified Lipoprotein The substance which can release the protection of the polymer relevant to the present invention for the specified lipoprotein to be used in the present invention may be the one having a property of being able to restore (regain) or stimulate the reaction of cholesterol in the lipoprotein, the reaction is inhibited by the polymer relevant to the present invention (the specified lipoprotein, which the reaction is inhibited by contacting the biological sample with the polymer relevant to the present invention).

The substances having such a property are, for example, one having the above described properties, therefore nonionic surfactant, anionic surfactant or amphoteric surfactant using in determination method (reagent) of total cholesterol per se can be used.

The nonionic surfactant includes, for example, polyoxyethylene alkyl ether [e.g. polyoxyethylene lauryl ether, polyoxyethylene cetyl ether, polyoxyethylene stearyl ether, polyoxyethylene oleyl ether, polyoxyethylene higher alcohol, etc.], polyoxyethylene alkyl aryl ether [e.g. polyoxyethylene octyl phenyl ether, polyoxyethylene nonyl phenyl ether, etc], polyoxyethylene fatty acid ester [e.g. polyethylene glycol monolaurate, polyethylene glycol monostearate, polyethylene glycol distearate, polyethylene glycol monooleate, etc.], polyoxyethylene sorbitan fatty acid ester [e.g. polyoxyethylene sorbitan monolaurate, polyoxyethylene sorbitan monopalmitate, polyoxyethylene sorbitan monostearate, polyoxyethylene sorbitan tristearate, polyoxyethylene sorbitan monooleate, polyoxyethylene sorbitan trioleate, etc.], sorbitan fatty acid ester [e.g. sorbitan monolaurate, sorbitan monopalmitate, sorbitan monostearate, sorbitan distearate, sorbitan tristearate, sorbitan monooleate, sorbitan trioleate, sorbitan sesquioleate, etc.], polyoxyethylene sorbitol fatty acid ester [e.g. tetraoleic acid polyoxyethylene sorbit, etc.], polyoxyethylene alkyl amine [e.g. polyoxyethylene lauryl amine, polyoxyethylene stearyl amine, etc.], or glycerin fatty acid ester [e.g. stearic acid monoglyceride, oleic acid monoglyceride, etc.].

The anionic surfactant includes, for example, cholic acid and derivatives thereof [e.g. cholic acid, deoxycholic acid, polyoxyethylene alkyl phenol ether sulfate, lauroylsarcosine, etc.].

The amphoteric surfactant includes, for example, betaine derivatives such as alkylbetaine derivatives [e.g. 2-alkyl-N-carboxymethyl-N-hydroxyethylimidazolinium betaine such as lauryl betaine, stearyl betaine, lauryldimethylammonium betaine, coconut betaine, palm oil fatty acid amide propyl betaine, lauryl amide propyl betaine, etc.]; imidazolinium betaine derivatives [e.g. 2-alkyl-N-carboxymethyl-N-hydroxyethylimidazolinium betaine such as 2-lauryl-N-carboxymethyl-N-hydroxyethylimidazolinium betaine, 2-undecyl-N-carboxymethyl-N-hydroxyethylimidazolinium betaine; 2-alkyl-N-carboxyethyl-N-hydroxyethylimidazolinium betaine, etc.] and sulfo betaine derivatives [e.g. N-octyl-N,N-dimethyl-3-ammonio-1-propanesulfonic acid, N-decyl-N,N-dimethyl-3-ammonio-1-propanesulfonic acid, N-dodecyl-N,N-dimethyl-3-ammonio-1-propanesulfonic acid, N-tetradecyl-N,N-dimethyl-3-ammonio-1-propanesulfonic acid, N-hexadecyl-N,N-dimethyl-3-ammonio-1-propanesulfonic acid, etc.]; for example, amino carboxylic acid derivatives such as alkylglycine, alkylbis(amino ethyl) glycine, dioctylpolyaminoethylglycine, N-alkylpolyamino ethylglycine and β-alanine derivativese; for example, imidazoline derivatives such as bis(2-undecyl-N-hydroxyethylimidazoline) chloracetic acid complex and alkylimidazoline derivatives; for example, amine oxide derivatives such as lauryldimethylamine oxide.

Among above described surfactants, nonionic surfactant and anionic surfactant are preferable.

The use concentration of the surface-active agent as described above may be the concentration which can restore (regain) or stimulate the reaction of cholesterol in the lipoprotein, which the reaction is inhibited by the polymer relevant to the present invention (the specified lipoprotein, which the reaction is inhibited by contacting the biological sample with the polymer relevant to the present invention), and it cannot be said flatly because the concentration may differ by the type and the use concentration of the polymer relevant to the present invention to be used and the type of the surface-active agent, and it may also differ by the ratio of the fluid volume between the first reagent solution and the second reagent solution when used in the 2 reagent solution method, however, the concentration thereof in the second reagent solution is usually 0.01-20% (w/v), preferably 0.05-5% (w/v).

These surface-active agents may be used alone or in combination of 2 types or more appropriately.

(14) Other Reagents

In the present invention, in addition to the reagents (constituent element) described above, the reagents usually used in this field may be available.

Such reagent includes, for example, agents avoiding from the influence of coexisting substance such as ascorbic acid, hemolysis and bilirubin (e.g. ascorbate oxidase, metal ion such as cupper ion and potassium ferrocyanide, etc.); an agent avoiding the influence of chyle by a hypertriglyceridemic specimen (e.g. surface-active agent, the salts such as NaCl and KCl, the enzymes such as LPL, etc.) and a reaction accelerator (e.g. surface-active agent, metal ion, etc.); the stabilizer of the enzymes (e.g. proteins such as bovine albumin, casein and gelatin, various types of amino acids such as glutamic acid, various types of sugars such as glucose, etc.); various types of salts (e.g. NaCl, calcium chloride, etc.); antioxidative substance (e.g. mannitol); chelating agent (e.g. EDTA); preservatives (e.g. sodium azide); adsorption-preventing agent [e.g. PMC polymer described in JP-A-2003-344413 such as PMPC, PMB82, PMB82-1M, PMB37, $PMC_{18}91$, $PMC_{18}82$ and $PMB_z82$, etc.].

The use concentration of other reagents as described above may be selected appropriately according to the method well known per se.

(15) Biological Sample

The biological sample to be applied by the present invention includes, for example, the biological sample such as serum and plasma, and the treated solution thereof obtained by dissolving and reconstituting appropriately in water, physiological saline or buffer solutions, usually used in this field, such as tris buffer, phosphate buffer, veronal buffer, borate buffer and Good's buffer.

3. Reagent and Kit of the Present Invention for Determining Cholesterol in the Lipoprotein The reagent and kit of the present invention are to be used for practicing the determination method of the present invention as described above; except for using the polymer relevant to the present invention, the reagents (constituent requisites) to be used for the method of determining cholesterol in the above described biological sample may be prepared so as to be contained within the rage usually used in this field; and the preferable embodiment and the use concentration of the constituent requisites are as described above.

In more specifically, the reagent and kit of the present invention are the ones which contain, for example, the following reagents (constituent requisites) as the main components, and may also contain reagents other than these.

(1) Reagent and Kit for the Direct Method

The reagent and kit for the direct method of the present invention as described above includes, for example, the ones which contain the following reagents (constituent requisites) as the main components:

The Reagent and Kit for the Direct Method (1) (a Single Reagent Solution Method)
    The polymer relevant to the present invention
    CHE
    co
    POD
    Oxidizable coloring agent (a coupler and a developer)
    Aqueous medium The Reagent and Kit for the Direct Method (1) (2 Reagent Solution Method)
(The First Reagent Solution)
    The polymer relevant to the present invention
    Aqueous medium
(The Second Reagent Solution)
    CHE
    CO
    Aqueous medium In the case described above, each POD, a coupler and a developer is contained in at least one of the first or the second reagent solution.

The Reagent and Kit for the Direct Method (2) (a Single Reagent Solution Method)
    The polymer relevant to the present invention
    CHE
    CHD
    NAD(P)
    Aqueous medium The Reagent and Kit for the Direct Method (2) (2 Reagent Solution Method)
(The First Reagent Solution)
    The polymer relevant to the present invention
    Aqueous medium
(The Second Reagent Solution)
    CHE
    CHD
    Aqueous medium In the case described above, NAD(P) is contained in at least one of the first or the second reagent solution.

(2) The Reagent and Kit for the Elimination Method (1)

The reagent and kit for the elimination method (1) of the present invention as described above includes, for example, the ones containing the following reagents (constituent requisites) as the main components:

The Reagent and Kit for the Elimination Method (1)-a (a Single Reagent Solution Method)
    The polymer relevant to the present invention
    CHE
    Co
    POD
    Oxidizable coloring agent (a coupler and a developer)
    Aqueous medium The Reagent and Kit for the Elimination Method (1)-b (a Single Reagent Solution Method)
    The polymer relevant to the present invention
    CHE
    CHD
    NAD(P)
    Aqueous medium The Reagent and Kit for the Elimination Method (1)-a (2 Reagent Solution Method)
(The First Reagent Solution)
    The polymer relevant to the present invention
    Aqueous medium
(The Second Reagent Solution)
    CHE
    CO
    Aqueous medium In the case described above, each POD, a coupler and a developer is contained in at least one of the first or the second reagent solution.

The Reagent and Kit for the Elimination Method (1)-a (2 Reagent Solution Method)
(The First Reagent Solution)
    The polymer relevant to the present invention
    CHE
    Co
    POD
    Coupler
    Developer
    Aqueous medium
(The Second Reagent Solution)
    A substance which can release the protection of the polymer relevant to the present invention for the specified lipoprotein (e.g. surface-active agent)
    Aqueous medium The Reagent and Kit for the Elimination Method (1)-b (2 Reagent Solution Method)
(The First Reagent Solution)
    The polymer relevant to the present invention
    Aqueous medium
(The Second Reagent Solution)
    CHE
    CHD
    Aqueous medium In the case described above, NAD(P) is contained in at least one of the first or the second reagent solution.

The Reagent and Kit for the Elimination Method (1)-b (2 Reagent Solution Method)
(The First Reagent Solution)
    The polymer relevant to the present invention
    CHE
    CHD
    NAD(P)
    Aqueous medium
(The Second Reagent Solution)
    A substance which can release the protection of the polymer relevant to the present invention for the specified lipoprotein (e.g. surface-active agent)
    Aqueous medium (3) The Reagent and Kit for the Elimination Method (2)

The reagent and kit for the elimination method (2) of the present invention as described above includes, for example, the ones which contain the following reagents (constituent requisites) as the main components:

The Reagent and Kit for the Elimination Method (2)-a (2 Reagent Solution Method)
(The First Reagent Solution)
    The polymer relevant to the present invention
    CHE
    Co
    POD Coupler or developer
Aqueous medium
(The Second Reagent Solution)
Developer or coupler
Aqueous medium
If needed, a substance which can release the protection of the polymer relevant to the present invention for the specified lipoprotein (e.g. surface-active agent)
In the case described above, CHE, CO and POD may be contained in both the first and the second reagent solution.
The Reagent and Kit for the Elimination Method (2)-a (2 Reagent Solution Method)
(The First Reagent Solution)
The polymer relevant to the present invention
CHE
CO
CAT
Aqueous medium
(The Second Reagent Solution)
CAT inhibitor
Aqueous medium
If needed, a substance which can release the protection of the polymer relevant to the present invention for the specified lipoprotein (e.g. surface-active agent)
In the case described above, each POD, a coupler and a developer is contained in at least one of the first or the second reagent solution, and in addition, CHE and CO may be contained in both the first and the second reagent solution.
The Reagent and Kit for the Elimination Method (2)-b (2 Reagent Solution Method)
(The First Reagent Solution)
The polymer relevant to the present invention
CHE
CO
POD
Coupler and/or developer
Aqueous medium
(The Second Reagent Solution)
CHD
NAD(P)
CO inhibitor
Aqueous medium
If needed, a substance which can release the protection of the polymer relevant to the present invention for the specified lipoprotein (e.g. surface-active agent)
In the case described above, CHE may be contained in both the first and the second reagent solution.
The Reagent and Kit for the Elimination Method (2)-b (2 Reagent Solution Method)
(The First Reagent Solution)
The polymer relevant to the present invention
CHE
CHD
NAD(P)
Aqueous medium
(The Second Reagent Solution)
Co
POD
CHD inhibitor
Oxidizable coloring agent (a coupler and a developer)
Aqueous medium
If needed, a substance which can release the protection of the polymer relevant to the present invention for the specified lipoprotein (for example, surface-active agent)
In the case described above, CHE may be contained in both the first and the second reagent solution.

In addition, the aforementioned kit may be combined with a standard preparation of the cholesterol in the measurement object of lipoprotein. For the aforementioned standard preparation, for example, the standard serum prepared using the serum and the like from human or animal, or the one derived from the same which contains the lipoprotein fraction of the measurement object may be used. Here, when using as the determination method the direct method of the present invention, the measurement object of lipoprotein means the lipoprotein other than the lipoprotein protected by the polymer relevant to the present invention (the lipoprotein other than the specified lipoprotein, which the reaction is inhibited by the polymer relevant to the present invention); and when the determination method utilized is the elimination method of the present invention, it means the lipoprotein protected by the polymer relevant to the present invention (the specified lipoprotein, which the reaction is inhibited by the polymer relevant to the present invention).

Further, an explanatory leaflet for the use in the determination method of the present invention described above may be contained in the kit. The aforementioned "explanatory leaflet" means an operation manual, a package insert or a pamphlet (leaflet) of the aforementioned kit in which the property, principle, operating procedure of the method of the present invention are substantially described in writing or with diagram.

Hereinafter, the present invention will be further explained in detail by referring to the following Examples, but the scope of the present invention should not be limited thereto.

EXAMPLE

The "compound (1)-(16)" means the compounds shown in the following Table 1.

TABLE 1

| Compound | Name | Structure |
|---|---|---|
| Compound (1) | Methacrylic acid | 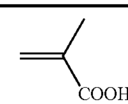 |
| Compound (2) | Acrylic acid | 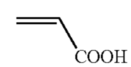 |
| Compound (3) | tert-Butyl methacrylate | 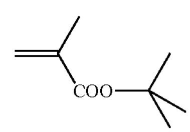 |
| Compound (4) | Dodecyl methacrylate | 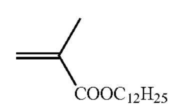 |
| Compound (5) | 2-Ethylhexyl methacrylate | 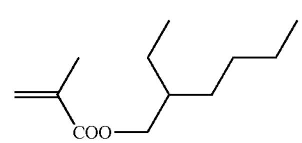 |
| Compound (6) | Bornanyl methacrylate | 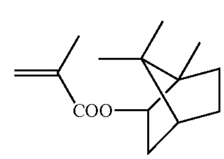 |

TABLE 1-continued

| Compound | Name | Structure |
|---|---|---|
| Compound (7) | Cyclohexyl methacrylate | CH2=C(CH3)-COO-C6H11 |
| Compound (8) | Cyclohexyl acrylate | CH2=CH-COO-C6H11 |
| Compound (9) | Heptadecylfluoro-octylethyl methacrylate | CH2=C(CH3)-COO(CH2)2(CF2)7CF3 |
| Compound (10) | 2,2,3,3,4,4,5,5-Octafluoro-pentyl methacrylate | CH2=C(CH3)-COOCH2(CF2)4H |
| Compound (11) | Cyclohexyl methacrylamide | CH2=C(CH3)-CONH-C6H11 |
| Compound (12) | Cyclohexyl vinyl ether | CH2=CH-O-C6H11 |
| Compound (13) | Vinylcyclohexyl | CH2=CH-C6H11 |
| Compound (14) | Allylcyclohexyl | CH2=CH-CH2-C6H11 |
| Compound (15) | Allylbenzene | CH2=CH-CH2-C6H5 |
| Compound (16) | Di(trifluoromethyl)methyl methacrylate | CH2=C(CH3)-COO-CH(CF3)2 |

Example 1

Preparation Method of the Polymer of the Present Invention

Example 1-1

After 23 g of methacrylic acid (manufactured by Wako Pure Chemical Industries Ltd.) [hereinafter, abbreviated as "monomer A"] and 23 g of cyclohexyl methacrylate (manufactured by Wako Pure Chemical Industries Ltd.)-[hereinafter, abbreviated as "monomer B"] are dissolved in 180 g of isopropanol, and 15 g of polymerization initiator (azo group-containing polyethylene glycol) [hereinafter abbreviated as "PEG"] (product name: VPE-0201, manufactured by Wako Pure Chemical Industries Ltd.) is added, the mixture was stirred under argon gas replacement at 78° C. for 6 hours. After finishing the reaction, the obtained reaction solution was poured into 500 ml of hexane, and then the supernatant fluid was removed. The precipitate was dried under reduced pressure, and thus, the polymer relevant to the present invention was obtained.

The polymer obtained was confirmed to have polymethacrylic acid segment (0.88 ppm to 1.96 ppm) and polyethylene glycol segment (3.58 ppm) by $^1$H-NMR spectrometry, and the presence of carbonyl group (—C=O) (1725 cm$^{-1}$) by IR spectrometry. The results were shown in Table 2.

Example 1-2 to 1-24

The polymer relevant to the present invention was prepared by conducting the same procedure as described in Example 1-1, except for using various types of monomers as monomer A and monomer B as shown in Table 2 at predefined ratio in the polymer of the present invention. The results were shown collectively in Table 2.

TABLE 2

| Example | Monomer A | Monomer B | Ratio by weight PEG | Ratio A | Ratio B | B/A | NMR spectrum | IR spectrum |
|---|---|---|---|---|---|---|---|---|
| 1-1 | (1) | (3) | 10 | 20 | 10 | 0.5 | 0.83~1.99 ppm(PMA), 3.56 ppm(PEG) | 1711 cm$^{-1}$(—C=O) |
| 1-2 | (1) | (7) | 10 | 20 | 10 | 0.5 | 0.908~2.02 ppm(PMA), 3.60 ppm(PEG) | 1724 cm$^{-1}$(—C=O) |
| 1-3 | (2) | (7) | 10 | 20 | 10 | 0.5 | 0.88~1.96 ppm(PMA), 3.59 ppm(PEG) | 1724 cm$^{-1}$(—C=O) |
| 1-4 | (1) | (7) | 10 | 40 | 20 | 0.5 | 0.84~2.10 ppm(PMA), 3.48 ppm(PEG) | 1726 cm$^{-1}$(—C=O) |
| 1-5 | (1) | (7) | 10 | 18 | 12 | 0.7 | 0.83~1.98 ppm(PMA), 3.58 ppm(PEG) | 1724 cm$^{-1}$(—C=O) |
| 1-6 | (1) | (7) | 10 | 17 | 13 | 0.8 | 0.94~1.90 ppm(PMA), 3.60 ppm(PEG) | 1725 cm$^{-1}$(—C=O) |
| 1-7 | (1) | (7) | 10 | 16 | 14 | 0.9 | 0.89~1.95 ppm(PMA), 3.55 ppm(PEG) | 1726 cm$^{-1}$(—C=O) |
| 1-8 | (1) | (7) | 10 | 15 | 15 | 1.0 | 0.88~1.96 ppm(PMA), 3.58 ppm(PEG) | 1727 cm$^{-1}$(—C=O) |
| 1-9 | (1) | (7) | 10 | 14 | 16 | 1.1 | 0.78~2.06 ppm(PMA), 3.59 ppm(PEG) | 1726 cm$^{-1}$(—C=O) |

TABLE 2-continued

| Example | Monomer A | Monomer B | Ratio by weight PEG | Ratio by weight A | Ratio by weight B | Ratio B/A | NMR spectrum | IR spectrum |
|---|---|---|---|---|---|---|---|---|
| 1-10 | (1) | (7) | 10 | 13 | 17 | 1.3 | 0.82~2.00 ppm(PMA), 3.56 ppm(PEG) | 1726 cm$^{-1}$(—C=O) |
| 1-11 | (1) | (7) | 10 | 12 | 18 | 1.5 | 0.87~1.97 ppm(PMA), 3.57 ppm(PEG) | 1724 cm$^{-1}$(—C=O) |
| 1-12 | (1) | (7) | 10 | 11 | 19 | 1.7 | 0.83~2.16 ppm(PMA), 3.58 ppm(PEG) | 1723 cm$^{-1}$(—C=O) |
| 1-13 | (1) | (4) | 10 | 10 | 20 | 2.0 | 0.80~2.08 ppm(PMA), 3.58 ppm(PEG) | 1729 cm$^{-1}$(—C=O) |
| 1-14 | (1) | (5) | 10 | 10 | 20 | 2.0 | 0.90~1.99 ppm(PMA), 3.60 ppm(PEG) | 1726 cm$^{-1}$(—C=O) |
| 1-15 | (1) | (6) | 10 | 10 | 20 | 2.0 | 0.78~2.03 ppm(PMA), 3.59 ppm(PEG) | 1723 cm$^{-1}$(—C=O) |
| 1-16 | (1) | (7) | 10 | 10 | 20 | 2.0 | 0.84~2.12 ppm(PMA), 3.60 ppm(PEG) | 1724 cm$^{-1}$(—C=O) |
| 1-17 | (1) | (7) | 10 | 10 | 30 | 3.0 | 0.80~2.00 ppm(PMA), 3.60 ppm(PEG) | 1725 cm$^{-1}$(—C=O) |
| 1-18 | (1) | (7) | 10 | 20 | 40 | 2.0 | 0.78~1.98 ppm(PMA), 3.53 ppm(PEG) | 1726 cm$^{-1}$(—C=O) |
| 1-19 | (1) | (8) | 10 | 20 | 40 | 2.0 | 0.80~2.01 ppm(PMA), 3.58 ppm(PEG) | 1729 cm$^{-1}$(—C=O) |
| 1-20 | (1) | (9) | 10 | 10 | 20 | 2.0 | 0.78~1.90 ppm(PMA), 3.58 ppm(PEG) | 1730 cm$^{-1}$(—C=O) |
| 1-21 | (1) | (10) | 10 | 10 | 20 | 2.0 | 0.86~1.90 ppm(PMA), 3.58 ppm(PEG) | 1732 cm$^{-1}$(—C=O) |
| 1-22 | (1) | (11) | 10 | 10 | 20 | 2.0 | 0.88~1.98 ppm(PMA), 3.57 ppm(PEG) | 1725 cm$^{-1}$(—C=O), 1633 cm$^{-1}$, 1525 cm$^{-1}$ (—CONH) |
| 1-23 | (1) | (12) | 10 | 10 | 20 | 2.0 | 0.90~2.12 ppm(PMA), 3.54 ppm(PEG) | 1727 cm$^{-1}$(—C=O) |
| 1-24 | (1) | (13) | 10 | 10 | 20 | 2.0 | 0.89~2.06 ppm(PMA), 3.58 ppm(PEG) | 1726 cm$^{-1}$(—C=O) |

※PMA: Polymethacrylic acid; PEG: Polyethylene glycol

Example 1-25 to 1-47

The polymer of the present invention was prepared by the same procedure as described in Example 1-1, except for using various types of monomers as monomer A and monomer B as shown in Table 3 at predefined ratio in the polymer of the present invention. The results were shown in Table 3.

TABLE 3

| Example | Monomer A | Monomer B | Ratio by weight PEG | Ratio by weight A | Ratio by weight B | Ratio B/A | NMR spectrum | IR spectrum |
|---|---|---|---|---|---|---|---|---|
| 1-25 | (1) | (14) | 10 | 10 | 20 | 2.0 | 0.88~1.90 ppm(PMA), 3.59 ppm(PEG) | 1727 cm$^{-1}$(—C=O) |
| 1-26 | (1) | (15) | 10 | 10 | 20 | 2.0 | 0.86~2.20 ppm(PMA), 3.58 ppm(PEG), 7.20 ppm(Ph) | 1725 cm$^{-1}$(—C=O) |
| 1-27 | (1) | (7) | 10 | 10 | 22 | 2.2 | 0.85~1.96 ppm(PMA), 3.55 ppm(PEG) | 1725 cm$^{-1}$(—C=O) |
| 1-28 | (1) | (7) | 10 | 10 | 24 | 2.4 | 0.90~1.92 ppm(PMA), 3.56 ppm(PEG) | 1726 cm$^{-1}$(—C=O) |
| 1-29 | (2) | (7) | 10 | 10 | 26 | 2.6 | 0.88~1.96 ppm(PMA), 3.59 ppm(PEG) | 1724 cm$^{-1}$(—C=O) |
| 1-30 | (1) | (7) | 10 | 10 | 28 | 2.8 | 0.83~2.00 ppm(PMA), 3.50 ppm(PEG) | 1726 cm$^{-1}$(—C=O) |
| 1-31 | (1) | (7) | 10 | 5 | 10 | 2.0 | 0.86~1.96 ppm(PMA), 3.58 ppm(PEG) | 1725 cm$^{-1}$(—C=O) |
| 1-32 | (1) | (8) | 10 | 10 | 20 | 2.0 | 0.90~2.01 ppm(PMA), 3.59 ppm(PEG) | 1725 cm$^{-1}$(—C=O) |
| 1-33 | (1) | (16) | 10 | 10 | 20 | 2.0 | 0.89~1.96 ppm(PMA), 3.57 ppm(PEG) | 1730 cm$^{-1}$(—C=O) |
| 1-34 | (1) | (7) | 10 | 10 | 20 | 2.0 | 0.84~1.90 ppm(PMA), 3.54 ppm(PEG) | 1725 cm$^{-1}$(—C=O) |
| 1-35 | (1) | (3) | 10 | 10 | 20 | 2.0 | 0.80~1.89 ppm(PMA), 3.58 ppm(PEG) | 1724 cm$^{-1}$(—C=O) |
| 1-36 | (1) | (3) | 10 | 40 | 20 | 0.5 | 0.89~2.02 ppm(PMA), 3.56 ppm(PEG) | 1724 cm$^{-1}$(—C=O) |
| 1-37 | (2) | (3) | 10 | 20 | 10 | 0.5 | 0.83~2.00 ppm(PMA), 3.60 ppm(PEG) | 1727 cm$^{-1}$(—C=O) |
| 1-38 | (1) | (3) | 20 | 30 | 30 | 1.0 | 0.88~2.13 ppm(PMA), 3.59 ppm(PEG) | 1726 cm$^{-1}$(—C=O) |

TABLE 3-continued

|  | Monomer | | Ratio by weight | | | Ratio | Physical property data | |
|---|---|---|---|---|---|---|---|---|
| Example | A | B | PEG | A | B | B/A | NMR spectrum | IR spectrum |
| 1-39 | (1) | (3) | 10 | 10 | 30 | 3.0 | 0.81~2.01 ppm(PMA), 3.61 ppm(PEG) | 1728 cm$^{-1}$(—C=O) |
| 1-40 | (2) | (3) | 20 | 30 | 30 | 1.0 | 0.99~2.02 ppm(PMA), 3.60 ppm(PEG) | 1726 cm$^{-1}$(—C=O) |
| 1-41 | (2) | (3) | 10 | 10 | 20 | 2.0 | 0.82~1.98 ppm(PMA), 3.56 ppm(PEG) | 1724 cm$^{-1}$(—C=O) |
| 1-42 | (2) | (3) | 10 | 10 | 30 | 3.0 | 0.84~2.00 ppm(PMA), 3.60 ppm(PEG) | 1724 cm$^{-1}$(—C=O) |
| 1-43 | (1) | (3) | 10 | 20 | 40 | 2.0 | 0.80~2.00 ppm(PMA), 3.59 ppm(PEG) | 1724 cm$^{-1}$(—C=O) |
| 1-44 | (1) | (3) | 20 | 10 | 20 | 2.0 | 0.80~1.98 ppm(PMA), 3.54 ppm(PEG) | 1724 cm$^{-1}$(—C=O) |
| 1-45 | (1) | (13) | 20 | 30 | 30 | 1.0 | 0.80~2.01 ppm(PMA), 3.58 ppm(PEG) | 1726 cm$^{-1}$(—C=O) |
| 1-46 | (1) | (11) | 20 | 30 | 30 | 1.0 | 0.84~1.94 ppm(PMA), 3.58 ppm(PEG) | 1726 cm$^{-1}$(—C=O), 1634 cm$^{-1}$, 1523 cm$^{-1}$ (—CONH) |
| 1-47 | (1) | (11) | 10 | 20 | 10 | 0.5 | 0.86~1.91 ppm(PMA), 3.58 ppm(PEG) | 1725 cm$^{-1}$(—C=O), 1635 cm$^{-1}$, 1526 cm$^{-1}$ (—CONH) |

※PMA: Polymethacrylic acid; PEG: Polyethylene glycol

Example 2-1

The reaction curve of the reaction between the reagent containing the polymer of the present invention for the cholesterol determination and various types of lipoprotein fractionated by ultracentrifugation method was determined, and the influence of the polymer of the present invention on the reactivity of the cholesterol in each lipoprotein was confirmed.

[Sample]

HDL fraction (cholesterol: 200 mg/dl), LDL fraction (cholesterol: 300 mg/dl) and VLDL fraction (cholesterol: 100 mg/dl) which were obtained by fractionation of human serum using ultracentrifugation method well known per se were each used as a sample.

[Reagent]

Reagent with the following composition was used.

| | |
|---|---|
| MOPS buffer (pH 7.0) | 25 mM |
| Sodium chloride | 0.40% |
| Cholesterol oxidase | 1 u/ml |
| Cholesterol esterase | 1 u/ml |
| HMMPS | 0.5 mM |
| 4-Aminoantipyrine | 1 mM |
| Peroxidase | 1.5 u/ml |
| The polymer of the present invention | 0.10% |

The polymers synthesized in Example 1-1 to 1-47 were used as the polymer of the present invention. In addition, as a control, the reagent not containing the polymer of the present invention was used.

[Measurement Condition]

Using Hitachi 7170 autoanalyzer (Manufactured by Hitachi Co., Ltd.), measurement was carried out by setting the measuring parameter as follows:

Measurement method: 1 point end [15]-[0];
Sample volume: 2.0 μl;
Reagent solution volume: 180 μl;
Measurement wave length: 700/600 nm;
Measurement temperature: 37° C.

[Result]

The time course of the reaction of each lipoprotein obtained by using a reagent not containing the polymer of the present invention was shown in FIG. 1; the time course of the reaction of each lipoprotein obtained by using a reagent containing the polymer of the present invention obtained in Example 1-1 was shown in FIG. 2; the time course of the reaction of each lipoprotein obtained by using a reagent containing the polymer of the present invention obtained in Example 1-3 was shown in FIG. 3; the time course of the reaction of each lipoprotein obtained by using a reagent containing the polymer of the present invention obtained in Example 1-8 was shown in FIG. 4; the time course of the reaction of each lipoprotein obtained by using a reagent containing the polymer of the present invention obtained in Example 1-11 was shown in FIG. 5; the time course of the reaction of each lipoprotein obtained by using a reagent containing the polymer of the present invention obtained in Example 1-16 was shown in FIG. 6; and the time course of the reaction of each lipoprotein obtained by using a reagent containing the polymer of the present invention obtained in Example 1-22 was shown in FIG. 7.

In addition, in each figure, -●- represents the results obtained for the HDL fraction sample (cholesterol: 200 mg/dl); -♦- represents the results obtained for the LDL fraction sample (cholesterol: 300 mg/dl); -■- represents the results obtained for the VLDL fraction sample (cholesterol: 100 mg/dl); and -Δ- represents the results obtained using physiological saline as the sample.

It can be understood that, from the results of FIG. 1 to FIG. 4, the reaction of cholesterol in LDL was inhibited when the reagent containing the polymer of the present invention prepared in Example 1-1, 1-3 and 1-8 was used; from the results shown in FIG. 1 and FIG. 5, the reaction of cholesterol in LDL and HDL was inhibited when the reagent containing the polymer of the present invention prepared in Example 1-11 was used; and from the results shown in FIG. 1 and FIG. 6 to FIG. 7, the reaction of cholesterol in HDL was inhibited when the reagent containing the polymer of the present invention prepared in Example 1-16 and 1-22 was used.

Although the results are not shown in the figure, it was each confirmed that the reaction of cholesterol in LDL was inhibited when the reagent containing the polymer of the present invention prepared in Example 1-2, 1-4 to 1-7, 1-36 to 1-38, 1-40 and 1-45 to 1-47 was used; the reaction of cholesterol in LDL and HDL was inhibited when the reagent containing the polymer of the present invention prepared in Example 1-9 to 1-12 was used; and the reaction of cholesterol in HDL was inhibited when the reagent containing the polymer of the present invention prepared in Example 1-13 to 1-15, 1-17 to 1-21, 1-23 to 1-26, 1-27 to 1-35, 1-39 and 1-41 to 1-44 was used.

From the results described above and Table 2 and Table 3, it was suggested that among the polymer of the present invention, the polymer in which the composition ratio between monomer unit (A) shown in the general formula [2] and monomer unit (B) shown in the general formula [3] was B/A≦1 (Example 1-1 to 1-8, 1-36 to 1-38, 1-40 and 1-45 to 1-47) protected LDL and had a property of inhibiting the reaction of cholesterol in LDL; among the polymer of the present invention, the polymer in which the composition ratio between these monomer units was 1<B/A<2 (Example 1-9 to 1-12) protected LDL and HDL and had a property of inhibiting the reaction of cholesterol in HDL and LDL; and the polymer in which the composition ratio between these monomer units was 2≦B/A (Example 1-13 to 1-35, 1-39 and 1-41 to 1-44) protected HDL and had a property of inhibiting the reaction of cholesterol in HDL.

Further, it was suggested that, by appropriate selection of these properties possessed by the polymer of the present invention, for example, the direct determination of cholesterol in the protected and specified lipoprotein, and the determination of cholesterol in the protected and specified lipoprotein after the cholesterol in the lipoprotein other than the specified lipoprotein protected by the polymer of the present invention is eliminated by the elimination method, are able to be performed.

Example 3-1

Measurement of HDL-Cholesterol by the Elimination Method

Using a polymer of the present invention having a property of inhibiting the reaction of cholesterol in HDL (the polymer prepared in Example 1-22), the HDL-cholesterol in the sample was measured by the elimination method, and compared with the measurement value obtained by the standard determination method of the UCHM method.
[Sample]
  Human serum: 20 specimens
  The triglyceride (TG) value in each human serum was measured using L-Type Wako TG-M (Manufactured by Wako Pure Chemical Industries Ltd.).
[UCMH Method]
  Measurement was carried out according to the method described in "Recommendations on Lipoprotein Measurement From the Working Group on Lipoprotein Measurement (NIH Publication No. 95-3044 September 1995 page 63-124)".
[Measurement of HDL-Cholesterol by the Present Invention]
(Reagent)
  Using the following reagent, the HDL-cholesterol in each sample was measured by the elimination method of the present invention.
  The First Reagent Solution

| | |
|---|---|
| MOPS buffer, pH 7.0 | 0.025 M |
| Sodium chloride | 0.30% |
| Cholesterol esterase | 2 u/ml |
| Cholesterol oxidase | 2 u/ml |
| Catalase | 1 ku/ml |
| The polymer of the present invention (Examples 1-22) | 0.25% |
| HMMPS | 0.5 mM |

The Second Reagent Solution

| | |
|---|---|
| MOPS buffer, pH 7.0 | 0.025 M |
| Peroxidase | 6 u/ml |
| 4-aminoantipyrine | 4 mM |
| Sodium azide | 0.10% |
| Nonionic surface-active agent | 2.00% |

(Measurement Condition)
  Using Olympus AU-640 autoanalyzer (Manufactured by Olympus Corporation), measurement was carried out by setting the measuring parameter as follows.
  It should be noted that, as a calibrator, the multicalibrator lipid (Manufactured by Wako Pure Chemical Industries Ltd.) was used.
  Condition: 2 point end method (photometric point: 10-27);
  Sample: 2 μl;
  The first reagent solution: 180 μl;
  The second reagent solution: 60 μl;
  Measurement wave length: main wave length: 600 nm; auxiliary wave length: 700 nm
[Result]
  The results of measurement and the TG value of each sample were shown in Table 4, and the correlation diagram between the method of the present invention and the UCMH method was shown in FIG. 8.
  The correlation equation and the correlation coefficient were as follows:

$y=1.03x-1.3444;$  Correlation equation $R^2=0.9742$  Correlation coefficient

TABLE 4

| | UCMH method: HDL-C measurement value | Method of the present invention: HDL-C measurement value | TG value |
|---|---|---|---|
| 1 | 47.0 | 44.9 | 594 |
| 2 | 37.0 | 37.8 | 709 |
| 3 | 32.3 | 31.8 | 546 |
| 4 | 50.2 | 50.9 | 884 |
| 5 | 31.4 | 30.2 | 1114 |
| 6 | 40.5 | 40.1 | 1465 |
| 7 | 38.3 | 34.6 | 527 |
| 8 | 40.2 | 41.0 | 563 |
| 9 | 35.9 | 36.3 | 514 |
| 10 | 30.6 | 30.4 | 1281 |
| 11 | 46.8 | 45.0 | 517 |
| 12 | 28.8 | 27.4 | 792 |
| 13 | 44.1 | 43.2 | 1176 |
| 14 | 45.5 | 45.4 | 507 |
| 15 | 48.8 | 50.1 | 802 |
| 16 | 46.1 | 48.0 | 688 |
| 17 | 41.3 | 42.2 | 462 |
| 18 | 22.0 | 22.6 | 1838 |
| 19 | 53.3 | 54.4 | 954 |
| 20 | 39.3 | 40.2 | 594 |
| mean | 40.0 | 39.8 | 826.4 |

As is clear from the results shown in Table 4 and FIG. 8, it is understandable that the method (reagent) for determining HDL-cholesterol by the elimination method of the present invention showed good correlation with the UCMH method of the standard determination method. Particularly, even with hypertriglyceridemic specimen, the value obtained by the method (reagent) for determining HDL-cholesterol by the elimination method of the present invention did not dissociate from the value obtained by the UCHM method, and both of the measurement values were identical.

Example 3-2

Measurement of LDL-Cholesterol by the Elimination Method

Using a polymer of the present invention having a property of inhibiting the reaction of cholesterol in the LDL (the polymer prepared in Example 1-8), the LDL-cholesterol in a sample was measured by the elimination method, and compared with the measurement value obtained by the UCHM method of the standard determination method.

[Sample]

Human serum: 20 specimens

The triglyceride (TG) value in each human serum was measured using L-Type Wako TG-M (Manufactured by Wako Pure Chemical Industries Ltd.).

[BQ Method]

Measurement was carried out according to the method described in "Recommendations on Lipoprotein Measurement From the Working Group on Lipoprotein Measurement (NIH Publication No. 95-3044 September 1995 page 1-62)".

[Measurement of LDL-Cholesterol by the Present Invention]

(Reagent)

Using the following reagent, the LDL-cholesterol in each sample was measured by the elimination method of the present invention.

The first reagent solution

| | |
|---|---|
| MOPS buffer, pH 7.0 | 0.025 M |
| Sodium chloride | 0.30% |
| Cholesterol esterase | 1 u/ml |
| Cholesterol oxidase | 2 u/ml |
| Catalase | 1 ku/ml |
| The polymer of the present invention (Example 1-8) | 0.25% |
| HMMPS | 1 mM |

The second reagent solution

| | |
|---|---|
| MOPS buffer, pH 7.0 | 0.025 M |
| Peroxidase | 5.0 u/ml |
| 4-aminoantipyrine | 4 mM |
| Sodiumazide | 0.10% |
| Nonionic surface-active agent | 1.20% |

(Measurement Condition)

Using Olympus AU-640 autoanalyzer (Manufactured by Olympus Corporation), measurement was carried out by setting the measuring parameter as follows.

As a calibrator, the Multicalibrator Lipid (Manufactured by Wako Pure Chemical Industries Ltd.) was used.

Condition: 2 point end method (photometric point: 10-27);
Sample: 2 μl;
The first reagent solution: 180 μl;
The second reagent solution: 60 μl
Measurement wave length: main wave length: 600 nm; auxiliary wave length: 700 nm;

[Result]

The results of measurement and the TG value of each sample were shown in Table 5, and the correlation diagram between the method of the present invention and the BQ method was shown in FIG. 9.

The correlation equation and the correlation coefficient were as follows:

$y=0.987x-1.1931$;     Correlation equation $R^2=0.9862$     Correlation coefficient

TABLE 5

| | BQ method: LDL-C measurement value | Method of the present invention: LDL-C measurement value | TG value |
|---|---|---|---|
| 1 | 47.6 | 45.8 | 546 |
| 2 | 134.5 | 128.6 | 720 |
| 3 | 69.4 | 66.6 | 635 |
| 4 | 152.4 | 155.5 | 569 |
| 5 | 70.4 | 67.5 | 693 |
| 6 | 53.6 | 51.5 | 681 |
| 7 | 112.5 | 107.6 | 477 |
| 8 | 152.4 | 148.0 | 577 |
| 9 | 51.4 | 52.8 | 587 |
| 10 | 100.3 | 101.2 | 1331 |
| 11 | 104.8 | 106.5 | 788 |
| 12 | 99.2 | 85.7 | 649 |
| 13 | 77.8 | 77.5 | 548 |
| 14 | 78.1 | 77.2 | 827 |
| 15 | 30.3 | 32.3 | 509 |
| 16 | 29.8 | 28.1 | 493 |
| 17 | 88.1 | 86.8 | 637 |
| 18 | 86.8 | 86.1 | 556 |
| 19 | 65.8 | 54.8 | 1020 |
| 20 | 87.6 | 86.9 | 496 |
| mean | 86.6 | 84.3 | 673.3 |

As is clear from the results shown in Table 5 and FIG. 9, it is understandable that the method (reagent) for determining LDL-cholesterol by the elimination method of the present invention showed good correlation with the BQ method of the standard determination method. Particularly, even with hypertriglyceridemic specimen, the value obtained by the method (reagent) for determining LDL-cholesterol by the elimination method of the present invention did not dissociate from the value obtained by the BQ method, and both of the measurement values were identical.

Even where 0.25% of PMB37 was additionally added to the first reagent solution and the same procedure was carried out; the LDL-cholesterol value showing good correlation with BQ measurement value was obtained; and such reagent was found not to affect on the determination method of the present invention.

Example 3-3

Measurement of VLDL-Cholesterol by the Direct Method

Using a polymer of the present invention having a property of inhibiting the reaction of cholesterol in LDL and HDL (the polymer prepared in Example 1-11), the VLDL-cholesterol in a sample was measured by the direct method, and compared with the measurement value obtained by the ultracentrifugation method of the standard determination method.

[Sample]

Human serum: 20 specimens

The triglyceride (TG) value in each human serum was measured using L-Type Wako TG-M (Manufactured by Wako Pure Chemical Industries Ltd.).

[Ultracentrifugation Method]

(1) Collection of VLDL Fraction by Ultracentrifugation Separation Method

The VLDL fraction was collected according to the method described in "Shin-Seikagaku Jikken Koza (Lectures on New Biochemical Experiment), 4. Shishitsu (Lipid) I, pp 197, (ed. Tokyo Kagaku Dojin)". That is, 2 ml of sodium chloride solution with the density d=1.006 was overlaid on a serum sample (4 ml), and centrifuged at 16° C., 20,000 rpm for 30 minutes; the chylomicron existing in the upper layer separated was removed; and then on to the remaining lower layer, additional 2 ml of sodium chloride solution with the density d=1.006 was overlaid and centrifuged at 16° C., 40,000 rpm for 18 hours; after that, the upper layer was collected and regarded as VLDL fraction.

(2) Measurement of VLDL-Cholesterol

The VLDL fraction obtained by the above procedure (1) was adjusted to the original serum volume of 4 ml by adding physiological saline, and using this solution as a sample, the cholesterol concentration in the sample was measured using a reagent for the measurement of total cholesterol (L-Type Wako CHO—H: manufactured by Wako Pure Chemical Industries Ltd.) and using Hitachi 7170 autoanalyzer (Manufactured by Hitachi Co., Ltd.) under the following measurement condition.

As a calibrator, the Multicalibrator Lipid (Manufactured by Wako Pure Chemical Industries Ltd.) was used.

Condition: 2 point end method (photometric point: 16-34);
Sample: 2 μl;
The first reagent solution: 180 μl;
The second reagent solution: 60 μl;
Measurement wave length: main wave length: 600 nm; auxiliary wave length: 700 nm;

[Measurement of VLDL-Cholesterol by the Present Invention]

(Reagent)

Using the following reagent, the VLDL-cholesterol in each sample was measured by the direct method of the present invention.

The first reagent solution

| | |
|---|---|
| MOPS buffer, pH 7.0 | 0.025 M |
| Sodium chloride | 0.10% |
| Polymer (the polymer obtained in Example 1-11) | 0.15% |
| HMMPS | 1 mM |

The second reagent solution

| | |
|---|---|
| MOPS buffer, pH 7.0 | 0.025 M |
| Cholesterol esterase | 2 u/ml |
| Cholesterol oxidase | 1 u/ml |
| Peroxidase | 10 u/ml |
| 4-aminoantipyrine | 2 mM |

(Measurement Condition)

Using Olympus AU-640 autoanalyzer (Manufactured by Olympus Corporation), measurement was carried out by setting the measuring parameter as follows.

As a calibrator, the Multicalibrator Lipid (Manufactured by Wako Pure Chemical Industries Ltd.) was used.

Condition: 2 point end method (photometric point: 10-27);
Sample: 3 μl;
The first reagent solution: 180 μl;
The second reagent solution: 60 μl
Measurement wave length: main wave length: 600 nm; auxiliary wave length: 700 nm;

[Result]

The results of measurement and the TG value of each sample were shown in Table 6, and the correlation diagram between the method of the present invention and the UCMH method was shown in FIG. 10.

The correlation equation and the correlation coefficient were as follows:

$$y=1.03x-1.3444;$$ Correlation equation $$R^2=0.9742$$ Correlation coefficient

TABLE 6

| | Ultracentrifugation method: VLDL-C measurement value | Method of the present invention: VLDL-C measurement value | TG value |
|---|---|---|---|
| 1 | 30.5 | 33.1 | 105 |
| 2 | 27.8 | 24.7 | 189 |
| 3 | 27.3 | 25.5 | 182 |
| 4 | 15.9 | 14.2 | 55 |
| 5 | 9.6 | 9.7 | 62 |
| 6 | 20.5 | 18.2 | 58 |
| 7 | 11.9 | 10.7 | 68 |
| 8 | 19.6 | 19.4 | 101 |
| 9 | 13.7 | 13.4 | 111 |
| 10 | 10.1 | 11.3 | 104 |
| 11 | 24.6 | 26.8 | 129 |
| 12 | 15.0 | 13.4 | 76 |
| 13 | 10.5 | 9.4 | 244 |
| 14 | 26.5 | 23.8 | 107 |
| 15 | 18.2 | 16.2 | 70 |
| 16 | 40.2 | 35.5 | 116 |
| 17 | 37.0 | 32.7 | 92 |
| 18 | 92.2 | 93.0 | 81 |
| 19 | 40.6 | 42.8 | 150 |
| 20 | 73.5 | 72.7 | 91 |
| mean | 28.3 | 27.3 | 109.6 |

As is clear from the results shown in Table 6 and FIG. 10, it is understandable that the method (reagent) for determining VLDL-cholesterol by the elimination method of the present invention showed good correlation with the ultracentrifugation method of the standard determination method. Even with hypertriglyceridemic specimen, the value obtained by the method (reagent) for determining VLDL-cholesterol by the direct method of the present invention did not dissociate from the value obtained by the ultracentrifugation method, and both of the measurement values were identical.

INDUSTRIAL APPLICABILITY

In the method for the direct determination of cholesterol in the lipoprotein, a specified lipoprotein is protected and the reaction of cholesterol in the aforementioned specified lipoprotein is inhibited, in other words, delayed or stopped temporarily by being coexisted with the polymer of the present invention, and the reaction of the cholesterol in the lipoprotein other than the specified lipoprotein is preceded preferentially, and thus, the cholesterol in the lipoprotein other than the specified lipoprotein can be determined. In addition, by preceding the reaction of the cholesterol and eliminating the same contained in the lipoprotein other than the specified lipoprotein, the cholesterol in the specified lipoprotein can be determined. By this procedure, the cholesterol in the objective lipoprotein can be determined without conducting separation and segregation of the lipoprotein other than the objective lipoprotein for the determination. Further, according to the present invention, it may be possible to provide a method and a reagent for determining cholesterol in the lipoprotein with excellent measurement accuracy in accord with the measurement value obtained by the standard determination method even for the problematic specimen with lipid abnormality.

BRIEF DESCRIPTION OF THE DRAWINGS

FIG. 1 is the time course of the reaction of each lipoprotein obtained in Example 2-1 using a reagent not containing the polymer of the present invention.

FIG. 2 is the time course of the reaction of each lipoprotein obtained in Example 2-1 using a reagent containing the polymer of the present invention obtained in Example 1-1.

FIG. 3 is the time course of the reaction of each lipoprotein obtained in Example 2-1 using a reagent containing the polymer of the present invention obtained in Example 1-3.

FIG. 4 is the time course of the reaction of each lipoprotein obtained in Example 2-1 using a reagent containing the polymer of the present invention obtained in Example 1-8.

FIG. 5 is the time course of the reaction of each lipoprotein obtained in Example 2-1 using a reagent containing the polymer of the present invention obtained in Example 1-11.

FIG. 6 is the time course of the reaction of each lipoprotein obtained in Example 2-1 using a reagent containing the polymer of the present invention obtained in Example 1-16.

FIG. 7 is the time course of the reaction of each lipoprotein obtained in Example 2-1 using a reagent containing the polymer of the present invention obtained in Example 1-22:

FIG. 8 is the correlation diagram between the measurement value of HDL-cholesterol by the method of the present invention and the measurement value of HDL-cholesterol by the UCMH method obtained in Example 3-1.

FIG. 9 is the correlation diagram between the measurement value of LDL-cholesterol by the method of the present invention and the measurement value of LDL-cholesterol by the BQ method obtained in Example 3-2.

FIG. 10 is the correlation diagram between the measurement value of VLDL-cholesterol by the method of the present invention and the measurement value of VLDL-cholesterol by the ultracentrifugation method obtained in Example 3-3.

DESCRIPTION OF REFERENCE NUMERALS

In FIG. 1 to 7, -●- represents the results obtained for the HDL fraction sample (cholesterol: 200 mg/dl); -♦- represents the results obtained for the LDL fraction sample (cholesterol: 300 mg/dl); -■- represents the results obtained for the VLDL fraction sample (cholesterol: 100 mg/dl); and -Δ- represents the results obtained using physiological saline as the sample.

What is claimed is:

1. A determination method of cholesterol in lipoprotein or lipoproteins (method (A)),
which measures an amount of cholesterol in the lipoproteins other than a specific lipoprotein(s) in a biological sample and comprises:
(a) contacting the biological sample in the presence of a polymer containing monomer units as constituents with a reagent group (1) comprising cholesterol esterase and cholesterol oxidase or a reagent group (2) comprising cholesterol esterase, cholesterol dehydrogenase, and NAD(P);
(b) measuring absorbance at least at a time after substantial completion of a reaction of cholesterol in lipoproteins other than the specific lipoprotein(s) in the biological sample in the presence of the polymer and before substantial initiation of a reaction of the cholesterol in the specific lipoprotein(s) in the biological sample with the reagent (1) or (2) in the presence of the polymer; and
(c) calculating the amount of cholesterol in the lipoproteins other than the specific lipoprotein(s) in the biological sample based on a value of the absorbance,
wherein the monomer units as the constituents of the polymer comprise:
a polyethylene glycol segment as the monomer unit represented by formula (1) (hereinafter abbreviated as PEG-Seg):

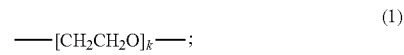

wherein, k represents an integer of 10 to 250;
a monomer unit represented by formula (2) (MU-A):

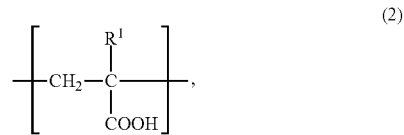

wherein, $R^1$ represents a hydrogen atom or $C_1$-$C_3$ alkyl group; and
a monomer unit represented by formula (3) (MU-B);

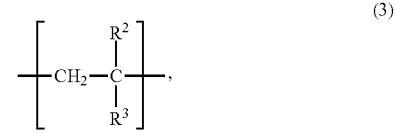

wherein, $R^2$ represents a hydrogen atom or $C_1$-$C_3$ alkyl group, and $R^3$ represents a group of formula (4):

wherein, $R^4$ represents an alkyl group, a haloalkyl group, a bornanyl group, an alkoxy group, an aralkyl group, or an alkylcarbamoyl group,
wherein the specific lipoprotein is high density lipoprotein (HDL), low density lipoprotein (LDL), or a combination of HDL and LDL,
wherein a) when the specific lipoprotein is HDL, a composition ratio by weight of an amount of the MU-A relative to an amount of the MU-B and a composition ratio by weight of a total amount of the MU-A and MU-B relative to an amount of the PEG-Seg in the polymer are:

2≦MU-*B*/MU-*A* and 1≦(MU-*A*+MU-*B*)/PEG-Seg≦10, b) when the specific lipoprotein is LDL, the composition ratios in the polymer are:

MU-B/MU-A≦1 and 1≦(MU-A+MU-B)/PEG-Seg≦10, and c) when the specific lipoproteins are a combination of HDL and LDL, the composition ratios in the polymer are:

1<MU-B/MU-A<2 and 1≦(MU-A+MU-B)/PEG-Seg≦10, and wherein the determination method does not include a step of separation or a step of isolation of the lipoprotein or the lipoproteins containing the cholesterol for which the amount is measured.

2. A determination method of cholesterol in lipoprotein or lipoproteins (method (B)), which measures an amount of cholesterol in the specific lipoprotein(s) in the biological sample and comprises:
(a) eliminating the cholesterol in the lipoproteins other than the specific lipoprotein(s) by contacting the biological sample in the presence of the polymer with a reagent group (1') comprising cholesterol esterase and cholesterol oxidase or a reagent group (2') comprising cholesterol esterase, cholesterol dehydrogenase, and NAD(P); and
(b) measuring absorbance at least two different time points, wherein the at least two different time points are time (1) after substantial completion of a reaction of the cholesterol in the lipoproteins other than the specific lipoprotein(s) in the biological sample with the reagent group (1') or (2') in the presence of the polymer and before substantial initiation of a reaction of cholesterol in the specific lipoprotein(s) in the biological sample with the reagent group (1') or (2') in the presence of the polymer, and time (2) after substantial completion of the reaction of the cholesterol in the specific lipoprotein(s) with the reagent group (1') or (2'); and
(c) calculating an amount of the cholesterol in the specific lipoprotein(s) in the biological sample based on values of the absorbance,
wherein the monomer units as the constituents of the polymer comprise:
a polyethylene glycol segment as the monomer unit represented by formula (1) (hereinafter abbreviated as PEG-Seg):

 (1)

wherein, k represents an integer of 10 to 250;
a monomer unit represented by formula (2) (MU-A):

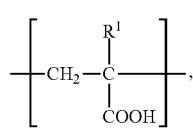 (2)

wherein, R$^1$ represents a hydrogen atom or C$_1$-C$_3$ alkyl group; and a monomer unit represented by formula (3) (MU-B):

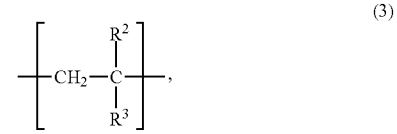 (3)

wherein, R$^2$ represents a hydrogen atom or C$_1$-C$_3$ alkyl group, and R$^3$ represents a group of formula (4):

 (4)

wherein, R$^4$ represents an alkyl group, a haloalkyl group, a bornanyl group, an alkoxy group, an aralkyl group, or an alkylcarbamoyl group,
wherein the specific lipoprotein is high density lipoprotein (HDL), low density lipoprotein (LDL), or a combination of HDL and LDL,
wherein a) when the specific lipoprotein is HDL, a composition ratio by weight of an amount of the MU-A relative to an amount of the MU-B and a composition ratio by weight of a total amount of the MU-A and MU-B relative to an amount of the PEG-Seg in the polymer are:

2≦MU-B/MU-A and 1≦(MU-A+MU-B)/PEG-Seg≦10, b) when the specific lipoprotein is LDL, the composition ratios in the polymer are:
MU-B/MU-A≦1 and 1≦(MU-A+MU-B)/PEG-Seg≦10, and
c) when the specific lipoproteins are a combination of HDL and LDL, the composition ratios in the polymer are:

1<MU-B/MU-A<2 and 1≦(MU-A+MU-F)/PEG-Seg≦10, and wherein the determination method does not include a step of separation or a step of isolation of the lipoprotein or the lipoproteins containing the cholesterol for which the amount is measured.

3. A determination method of cholesterol in lipoprotein or lipoproteins (method (C)), which measures an amount of the cholesterol in the specific lipoprotein(s) in the biological sample and comprises:
(a) eliminating the cholesterol in the lipoproteins other than the specific lipoprotein(s), in the presence of the polymer, by contacting the biological sample with a reagent or reagents for eliminating the cholesterol in the lipoproteins other than the specific lipoprotein(s);
(b) contacting the biological sample with a reagent group (1") comprising cholesterol esterase and cholesterol oxidase or a reagent group (2") comprising cholesterol esterase, cholesterol dehydrogenase, and NAD(P);
(c) measuring absorbance at least at a time point after substantial completion of a reaction of the cholesterol in the specific lipoprotein(s) in the biological sample with the reagent group (1") or (2") in the presence of the polymer; and
(d) calculating an amount of the cholesterol in, the specific lipoprotein(s) in the biological sample based on a value of the absorbance, wherein the reagent or reagents for eliminating the cholesterol in the lipoproteins other than the specific lipoprotein(s) are different from the reagent groups (1") and (2"), and wherein the monomer units as the constituents of the polymer comprise:

a polyethylene glycol segment as the monomer unit represented by formula (1) (hereinafter abbreviated as PEG-Seg):

(1)

wherein, k represents an integer of 10 to 250;
a monomer unit represented by formula (2) (MU-A):

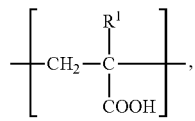
(2)

wherein, $R^1$ represents a hydrogen atom or $C_1$-$C_3$ alkyl group; and
a monomer unit represented by formula (3) (MU-B):

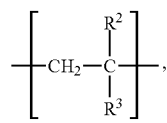
(3)

wherein, $R^2$ represents a hydrogen, atom or $C_1$-$C_3$ alkyl group, and $R^3$ represents a group of formula (4):

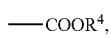
(4)

wherein, $R^4$ represents an alkyl group, a haloalkyl group, a bornanyl group, an alkoxy group, an aralkyl group, or an alkylcarbamoyl group, wherein the specific lipoprotein is high density lipoprotein (HDL) low density lipoprotein (LDL), or a combination of HDL and LDL, wherein a) when the specific lipoprotein is HDL, a composition ratio by weight of an amount of the MU-A relative to an amount of the MU-B and a composition ratio by weight of a total amount of the MU-A and MU-B relative to an amount of the PEG-Seg in the polymer are:

2≦MU-$B$/MU-$A$ and 1≦(MU-$A$+MU-$B$)/PEG-Seg≦10 b) when the specific lipoprotein is LDL, the composition ratios in the polymer are:

MU-$B$/MU-$A$≦1 and 1≦(MU-$A$+MU-$B$)/PEG-Seg≦10, and c) when the specific lipoproteins are a combination of HDL and LDL, the composition ratios in the polymer are:

1<MU-$B$/MU-$A$<2 and 1≦(MU-$A$+MU-$B$)/PEG-Seg≦10, and wherein the determination method does not include a step of separation or a step of isolation of the lipoprotein or the lipoproteins containing the cholesterol for which the amount is measured.

4. The determination method according to claim 1, claim 2, or claim 3, wherein the PEG-Seg is represented by formula (5):

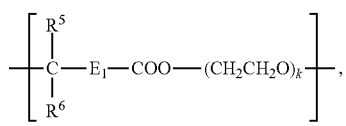
(5)

wherein, $R^5$ represents a hydrogen atom or $C_1$-$C_3$ alkyl group, $R^6$ represents a cyano group or $C_1$-$C_3$ alkyl group, $E_1$ represents $C_1$-$C_6$ alkylene group, and k represents an integer of 10 to 250.

5. The determination method according to claim 1, claim 2, or claim 3 wherein the polymer is represented by formula (6):

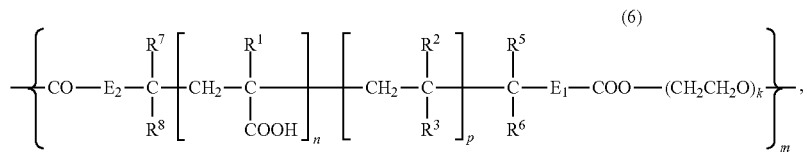
(6)

wherein, $R^5$ and $R^7$ each independently represent a hydrogen atom or $C_1$-$C_3$ alkyl group, $R^6$ and $R^8$ each independently represent a cyano group or $C_1$-$C_3$ alkyl group, $E_1$ and $E_2$ each independently represent $C_1$-$C_6$ alkylene group, n represents an integer of 50 to 900, p represents an integer of 50 to 900, m represents an integer of 1 to 10, and $R^1$ to $R^3$ and k are the same as described in claim 1, claim 2, or claim 3, respectively.

6. The determination method according to claim 1, claim 2, or claim 3, wherein the MU-B is derived from tert-butyl methacrylate, cyclohexyl methacrylate, 2-ethylhexyl methacrylate, dodecyl methacrylate, bornyl methacrylate, di(trifluoromethyl)methyl methacrylate, 2,2,3,3,4,4,5,5-octafluoropentyl methacrylate, heptadecafluorooctylethyl methacrylate, cyclohexyl methacrylamide, cyclohexyl acrylate, vinylcyclohexyl, allylcyclohexyl, cyclohexyl vinyl ether, or allylbenzene.

7. The determination method according to claim 1, claim 2 or claim 3, wherein the average molecular weight of the polymer is 10,000 to 120,000.

8. The determination method according to claim 1, claim 2, or claim 3, wherein the MU-A is derived from methacrylic acid, and the MU-B is derived from cyclohexyl methacrylate.

9. The determination method according to claim 1, claim 2, or claim 3, wherein the reagent for eliminating cholesterol in the lipoprotein(s) other than the specific lipoprotein(s) in the method (C) comprises a combination of cholesterol esterase, cholesterol oxidase, and peroxidase with a coupler, or a developer, or catalase.

10. The determination method according to claim 1, claim 2, or claim 3, wherein, in the method (A), the method (B) or the method (C), respectively, the specific lipoprotein(s) is high density lipoprotein (HDL), low density lipoprotein (LDL), or a combination of HDL and LDL.

11. The determination method according to claim 1, claim 2, or claim 3, wherein the specific lipoprotein is the HDL, and the composition ratios in, the polymer are:

$2 \leq \text{MU-}B/\text{MU-}A$ and $1 \leq (\text{MU-}A+\text{MU-}B)/\text{PEG-Seg} \leq 10$.

12. The determination method according to claim 1, claim 2, or claim 3, wherein the specific lipoprotein is the LDL, and the composition ratios in the polymer are:

$\text{MU-}B/\text{MU-}A \leq 1$ and $1 \leq (\text{MU-}A+\text{MU-}B)/\text{PEG-Seg} \leq 10$.

13. The determination method according to claim 1, claim 2, or claim 3, wherein the specific lipoproteins are the HDL and the LDL, and the composition ratios in the polymer are:

$1 < \text{MU-}B/\text{MU-}A < 2$ and $1 \leq (\text{MU-}A+\text{MU-}B)/\text{PEG-Seg} \leq 10$.

* * * * *